United States Patent
Sacks et al.

(10) Patent No.: US 9,494,606 B2
(45) Date of Patent: Nov. 15, 2016

(54) QUANTIFICATION OF LIPOPROTEINS

(71) Applicant: President and Fellows of Harvard College, Cambridge, MA (US)

(72) Inventors: Frank M. Sacks, Belmont, MA (US); Jeremy D. Furtado, Berkley, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/399,737

(22) PCT Filed: May 9, 2013

(86) PCT No.: PCT/US2013/040385
§ 371 (c)(1),
(2) Date: Nov. 7, 2014

(87) PCT Pub. No.: WO2013/170057
PCT Pub. Date: Nov. 14, 2013

(65) Prior Publication Data
US 2015/0168427 A1 Jun. 18, 2015

Related U.S. Application Data

(60) Provisional application No. 61/644,995, filed on May 9, 2012, provisional application No. 61/649,898, filed on May 21, 2012, provisional application No. 61/779,852, filed on Mar. 13, 2013.

(51) Int. Cl.
*G01N 33/53* (2006.01)
*G01N 33/92* (2006.01)
(52) U.S. Cl.
CPC ......... G01N 33/92 (2013.01); *G01N 2333/775* (2013.01)

(58) Field of Classification Search
None
See application file for complete search history.

(56) References Cited

U.S. PATENT DOCUMENTS

| | | | |
|---|---|---|---|
| 5,236,830 A | 8/1993 | Ishikawa | |
| 5,989,806 A | 11/1999 | Brust | |
| 6,423,830 B1 * | 7/2002 | Winge | C07K 14/755 530/359 |
| 7,098,036 B2 * | 8/2006 | Koren | C07K 16/18 435/7.1 |
| 2002/0098597 A1 | 7/2002 | Koren et al. | |
| 2004/0115725 A1 * | 6/2004 | Pieper | G01N 30/14 435/7.1 |
| 2009/0286960 A1 * | 11/2009 | Hoang | C07K 14/775 530/359 |

OTHER PUBLICATIONS

James et al., Immunoaffinity fractionation of high-density lipoprotein subclasses 2 and 3 using anti-apolipoprotein A-I and A-II immunosorbent gels. Biochim Biophys Acta. Apr. 26, 1989;1002(3):292-301.

\* cited by examiner

*Primary Examiner* — Gary W Counts
(74) *Attorney, Agent, or Firm* — Wolf, Greenfield & Sacks, P.C.

(57) ABSTRACT

Some aspects of this disclosure provide methods and reagents for the detection of apolipoproteins in a sample, for example, a sample obtained from a human subject. Some aspects of this disclosure provide protocols and reagents for the quantification of lipoproteins and lipoprotein particle populations comprising specific combinations of non-integral apolipoproteins and integral apolipoproteins, which is useful, inter alia, for the detection of diseases such as cardiovascular disease as well as an assessment of the risk of an individual to develop a disease.

4 Claims, 5 Drawing Sheets

QUANTIFICATION OF LIPOPROTEINS

RELATED APPLICATIONS

This application is a national stage filing under 35 U.S.C. 371 of International Application PCT/US2013/040385, filed May 9, 2013, which claims the benefit of the filing under 35 U.S.C. §119(e) of U.S. Provisional Application Ser. No. 61/644,995, filed on May 9, 2012, U.S. Provisional Application Ser. No. 61/649,898, filed on May 21, 2012, and U.S. Provisional Application Ser. No. 61/779,852, filed on Mar. 13, 2013, the contents of all of which are incorporated by reference in their entirety. International Application PCT/US2013/040385 was published under PCT Article 21(2) in English.

BACKGROUND

Lipoproteins are particles comprising apolipoproteins and lipids, such as triacylglycerols and cholesterol. In recent years, a differentiated view of the health benefits and risks conferred by different types of lipoproteins, such as high-density lipoproteins and low-density lipoproteins, has emerged. While essential for lipid transport through the aqueous circulation, certain types of lipoproteins (sometimes referred to as "bad cholesterol") have been suggested to contribute to disease and to increase the risk of disease, including, but not limited to, cardiovascular disease, while other types of lipoproteins (sometimes referred to as "good cholesterol") have been determined to confer health benefits. Current methods for high-resolution lipoprotein analysis, e.g., the analysis of the apolipoprotein content and of subpopulations of lipoprotein particles comprising specific apolipoprotein combinations in a given population of lipoproteins, cannot be applied on a large scale required for epidemiological studies or for routine application in clinical diagnostics, because they are time-intensive and cost-prohibitive.

SUMMARY

Some aspects of this disclosure are based on the recognition that the quantitative analysis of the apolipoprotein content of lipoprotein particles is emerging as a powerful diagnostic tool, as research elucidates the effects of particular apolipoproteins on lipoprotein metabolism and cardiovascular disease risk. Some aspects of this disclosure are based on the recognition that current methods for quantifying lipids and lipoproteins with and without non-integral apolipoproteins are both time-consuming and expensive.

The lipoproteins that circulate in blood in humans are divided into two categories defined by their specific integral apolipoprotein—apo A-1 (or apoA-I) lipoproteins and apoB lipoproteins. See, e.g., Alaupovic P. *Significance of apolipoproteins for structure, function, and classification of plasma lipoproteins*. Methods Enzymol. 1996; 263:32-60. ApoA-I lipoproteins are commonly called high density lipoproteins (HDL), and apoB lipoproteins include chylomicrons, very low density lipoproteins, intermediate density lipoproteins, low density lipoproteins, and lipoprotein(a). The function of lipoproteins is to transport lipids that are not soluble in blood from their sites of synthesis or absorption to other tissues for metabolism into energy, storage of energy, or conversion to hormones and to other bioactive molecules. Cholesterol, cholesterol ester, triglycerides, and phospholipids are the principal lipids that are transported in lipoproteins. The integral apolipoproteins are termed as such because they are essential for the synthesis of lipoproteins by the intestine and liver, and provide to the lipoproteins essential metabolic functions. ApoA-I is the integral apolipoprotein of HDL, and it is an activator of reverse cholesterol transport, the principal function of HDL that removes cholesterol from tissues including arteries containing atherosclerosis, packages the cholesterol in the HDL particle, and delivers it to the liver for excretion. Although a small amount of the HDL in blood may lack apoA-I, perhaps transiently, HDL concentration is commonly measured by its apoA-I concentration in blood, and a high apoA-I concentration is a strong indicator of low risk of cardiovascular disease. ApoB is essential for the intestinal cell to package and absorb dietary fat and fat-soluble vitamins, and for the liver to package and secrete into the blood circulation cholesterol and triglyceride. There can be no chylomicrons, VLDL, LDL, or lipoprotein(a) without apoB. The concentration of apoB in blood is a strong predictor of risk of cardiovascular disease. A non-integral apolipoproteins is an apolipoproteins that is present on a lipoprotein but not required for its synthesis in the liver or intestine or its secretion into the blood circulation. The non-integral apolipoproteins regulate the metabolism of the lipoproteins once they are secreted into blood, for example by targeting the lipoproteins for uptake by specific cells (e.g. apoE) or by blocking lipoprotein clearance from plasma (e.g. apoC-III). Non-integral apolipoproteins also affect the risk of cardiovascular disease. The current state-of-the-art methods typically involve fractionation of lipoproteins into those containing and those deficient of a non-integral apolipoprotein of interest using immuno-affinity chromatography and subsequent elution, concentration, and quantification via a sandwich ELISA. Such immuno-affinity chromatography methods take multiple days to perform and are also costly, which has proven prohibitive for use in large epidemiological cohorts or as standard clinical diagnostic assays. See, e.g., Khoo C, Campos H, Judge H, Sacks F M. *Effects of estrogenic oral contraceptives on the lipoprotein B particle system defined by apolipoproteins E and C-III content*. J Lipid Res. 1999 February; 40(2):202-12, the entire contents of which are incorporated by reference herein.

Some aspects of this disclosure relate to the surprising discovery that quantification of lipoprotein particles based on their apolipoprotein content can be achieved by a modified sandwich ELISA technology that obviates the time-consuming and costly immuno-affinity chromatography methodology, resulting in a quantitative assay that is technically easier, faster, and less expensive to perform than the current standard methods. The technology described herein can be used to quantify lipoproteins based on their apolipoprotein content, and can also be extended to the analysis of additional analytes of interest that are comprised in or on lipoprotein particles.

In some embodiments, the technology provided herein comprises binding of lipoprotein particles in a sample that comprise an analyte of interest, e.g., an integral apolipoprotein (e.g. apoA-I, apoB), a non-integral apolipoprotein (e.g., apoA-II, apoA-IV, apoA-V, apoC-I, apoC-II, apoC-III, apoC-IV, apoD, apoE, apoH, apoJ, and/or apo-L), or a lipid molecule (e.g., a phospholipid or a modified lipid molecule (e.g., modified by oxidative processes in vivo)) to a solid support, for example, to the surface of a well of an ELISA plate coated with an antibody specifically binding the analyte. Unbound lipoprotein particles, which are deficient in the analyte, remain in solution and can be removed and quantified. Bound lipoproteins, comprising the analyte of interest, remain on the solid support and can, in some embodiments, directly be quantified on the support (e.g., via sandwich ELISA), thus obviating any further transfer, elution, and concentration steps. It will be apparent to those of skill in the art that the technology provided herein is not limited to apolipoproteins and lipids, but can be used to quantify lipoprotein particles comprising any analyte that can be bound to a solid support with a suitable binding agent, for example, an antibody or antibody fragment specifically binding the analyte. It will be apparent to those of skill in the art that the technology provided herein is not limited to the analytes that are expressly described herein. The technology is applicable to any analyte of interest that is bound to or otherwise associated with a lipoprotein and that is specifically bound by a binding agent.

Some embodiments of this disclosure provide a method of detecting an apolipoprotein in a sample. In some embodiments, the method comprises (a) contacting a sample comprising a lipoprotein particle with a binding agent that specifically binds a non-integral apolipoprotein, thereby depleting the sample of the non-integral apolipoprotein; (b) contacting the sample depleted of the non-integral apolipoprotein with a binding agent that specifically binds an integral apolipoprotein; (c) detecting an integral apolipoprotein in or on a lipoprotein particle bound to the binding agent of (a) and/or detecting an integral apolipoprotein in or on a lipoprotein particle bound to the binding agent of (b). In some embodiments, depleting the sample of the non-integral apolipoprotein comprises depleting the sample of lipoprotein particles comprising the non-integral apolipoprotein. In some embodiments, the non-integral apolipoprotein is a protein described in Table 2. In some embodiments, the non-integral apolipoprotein is selected from the group consisting of apoA-II, apoA-IV, apoA-V, apoC-I, apoC-II, apoC-III, apoC-IV, apoD, apoE, apoH, and apoJ. In some embodiments, the integral apolipoprotein is selected from the group consisting of apoA-I and apoB. In some embodiments, the method comprises repeating (a), and wherein the binding agent used in repeating (a) specifically binds an apolipoprotein different from the apolipoprotein of any previous (a). In some embodiments, the apolipoprotein bound to the binding agent of (a) is not separated from the binding agent of (a) prior to the detecting. In some embodiments, the apolipoprotein bound to the binding agent of (b) is not separated from the binding agent of (b) prior to the detecting. In some embodiments, the detecting comprises contacting the lipoprotein particles comprising the apolipoprotein bound to the binding agent of (a) and/or the lipoprotein particles comprising the apolipoprotein bound to the binding agent of (b) with a detection agent. In some embodiments, the detection agent of (a) is identical to the detection agent of (b). In some embodiments, the detection agent specifically binds to an apolipoprotein. In some embodiments, the detection agent specifically binds to an integral apolipoprotein. In some embodiments, the detection agent specifically binds to a non-integral apolipoprotein. In some embodiments, the detection agent comprises an antibody or an antigen-binding fragment thereof. In some embodiments, the detection agent comprises a detectable label. In some embodiments, the detectable label is selected from the group consisting of a fluorescent moiety, a tag, an enzyme, and a radioisotope. In some embodiments, the detecting is via an enzyme-linked immunosorbent assay (ELISA). In some embodiments, the ELISA is a sandwich ELISA. In some embodiments, the binding agent of (a) and/or the binding agent of (b) comprises an antibody or an antigen-binding antibody fragment. In some embodiments, the binding agent of (a) and/or the binding agent of (b) is conjugated to a solid support. In some embodiments, the solid support is a surface of a bead, of a test tube, or of a plate well. In some embodiments, the bead, the test tube, or the plate well is suitable for ELISA. In some embodiments, the detecting further comprises quantifying. In some embodiments, the method comprises calculating a ratio of (i) the quantity of lipoprotein particles comprising the integral apolipoprotein bound to the binding agent of (a) to (ii) the quantity of lipoprotein particles comprising the integral apolipoprotein bound to the binding agent of (b). In some embodiments, the method further comprises measuring a level of an analyte in a lipoprotein particle bound to the binding agent of (a) and/or a lipoprotein particle bound to a lipoprotein particle of (b). In some embodiments, the analyte is a lipid. In some embodiments, the analyte is cholesterol or a triacylglyceride or a phospholipid.

Some aspects of this disclosure provide a method of detecting an analyte in or on a lipoprotein particle in a sample. In some embodiments, the method comprises (a) depleting the sample of any undesired lipoprotein particles; (b) contacting the sample with a binding agent that specifically binds a component of a lipoprotein particle, thereby depleting the sample of the component; (c) separating a lipoprotein particle bound to the binding agent of (b) from the remainder of the sample; and (d) subjecting a lipoprotein particle bound to the binding agent of (b) and/or a lipoprotein particle comprised in the remainder of the sample of (c) to an assay detecting the analyte. In some embodiments, the depleting of (a) comprises immunoprecipitation of the undesired lipoprotein particles. In some embodiments, the depleting of (a) comprises contacting the sample with a binding agent specifically binding a molecule comprised in the undesired lipoprotein particles. In some embodiments, the molecule is an apolipoprotein. In some embodiments, the molecule is an apolipoprotein identified in Table 2. In some embodiments, the undesired lipoprotein particles comprise apoB. In some embodiments, the undesired lipoprotein particles comprise apoA-I. In some embodiments, the analyte is a lipid. In some embodiments, the lipid is cholesterol, a cholesterol derivative, or a triacylglyceride. In some embodiments, the assay is an ELISA.

Some aspects of this disclosure provide a method of detecting an apolipoprotein in a sample. In some embodiments, the method comprises (a) contacting a sample comprising a lipoprotein particle with a binding agent that specifically binds a non-integral apolipoprotein, thereby depleting the sample of the non-integral apolipoprotein; (b) contacting the sample depleted of the non-integral apolipoprotein with a binding agent that specifically binds an integral apolipoprotein; (c) dissociating a lipoprotein particle bound to the binding agent of (a); (d) contacting the dissociated components of the lipoprotein particle of (c) with a binding agent that specifically binds an integral apolipoprotein; and (e) detecting an apolipoprotein in or on a lipoprotein particle bound to the binding agent of (b) and/or an apolipoprotein bound to the binding agent of (d). In some embodiments, depleting the sample of the non-integral apolipoprotein comprises depleting the sample of lipoprotein particles comprising the non-integral apolipoprotein. In some embodiments, the non-integral apolipoprotein is a protein described in Table 2. In some embodiments, the non-integral apolipoprotein is selected from the group consisting of apoA-II, apoA-IV, apoA-V, apoC-I, apoC-II, apoC-III, apoC-IV, apoD, apoE, apoH, and apoJ. In some embodiments, the integral apolipoprotein is selected from the group consisting of apoA-I and apoB. In some embodiments, the binding agents of (b) and (d) are identical. In some embodiments, the dissociating comprises contacting the lipoprotein particles bound to the binding agent of (a) with a detergent. In some embodiments, the detergent is TWEEN 20™. In some embodiments, the detecting comprises contacting the lipoprotein particles comprising the apolipoprotein bound to the binding agent of (b) and/or the apolipoprotein bound to the binding agent of (d) with a detection agent. In some embodiments, the detection agent for detecting the lipoprotein particles comprising the apolipoprotein bound to the binding agent of (b) is identical to the detection agent for detecting the apolipoprotein bound to the binding agent of (d). In some embodiments, the detection agent specifically binds an integral apolipoprotein. In some embodiments, the detection agent specifically binds a non-integral apolipoprotein. In some embodiments, the detection agent comprises an antibody or an antigen-binding fragment thereof. In some embodiments, the detecting is via an enzyme-linked immunosorbent assay (ELISA). In some embodiments, the ELISA is a sandwich ELISA. In some embodiments, the binding agent of (a), the binding agent of (b), and/or the binding agent of (d) comprises an antibody or an antigen-binding antibody fragment. In some embodiments, the binding agent of (a), the binding agent of (b), and/or the binding agent of (d) is conjugated to a solid support. In some embodiments, the solid support is a surface of a bead, of a test tube, or of a plate well. In some embodiments, the bead, the test tube, or the plate well is suitable for ELISA. In some embodiments, the method further comprises quantifying the lipoprotein particles comprising the apolipoprotein bound to the binding agent of (b) and/or the apolipoprotein bound to the binding agent of (d). In some embodiments, the method further comprises calculating a ratio of (i) the lipoprotein particles comprising the apolipoprotein bound to the binding agent of (b) and (ii) the apolipoprotein bound to the binding agent of (d). In some embodiments, the method further comprises measuring a level of an analyte in a lipoprotein particle bound to the binding agent of (b) and/or in a lipoprotein particle bound to a lipoprotein particle of (d). In some embodiments, the analyte is a lipid. In some embodiments, the analyte is cholesterol or a triacylglyceride or a phospholipid.

Some aspects of this invention provide an enzyme-linked immunosorbent assay (ELISA) plate for detecting an apolipoprotein. In some embodiments, the plate comprises (a) one or more wells, and (b) a binding agent that specifically binds a non-integral apolipoprotein, wherein the binding agent is conjugated to a surface of the one or more wells of (a). In some embodiments, the non-integral apolipoprotein is a protein described in Table 2. In some embodiments, the non-integral apolipoprotein is selected from the group consisting of apoA-II, apoA-IV, apoA-V, apoC-I, apoC-II, apoC-III, apoC-IV, apoD, apoE, apoH, and apoJ. Some aspects of this disclosure provide an ELISA plate for detecting an apolipoprotein. In some embodiments, the plate comprises (a) one or more wells, and (b) a binding agent that specifically binds an integral apolipoprotein, wherein the binding agent is conjugated to a surface of the one or more wells of (a). In some embodiments, the integral apolipoprotein is selected from the group consisting of (apo)A-I and apoB. In some embodiments, the binding agent is an antibody or an antigen-binding antibody fragment.

Some aspects of this disclosure provide a kit, comprising an ELISA plate as described herein. In some embodiments, the kit further comprises a detection agent. In some embodiments, the kit comprises a detection agent that specifically binds an apolipoprotein; a detection agent that specifically binds to an integral apolipoprotein; and/or a detection agent that specifically binds to a non-integral apolipoprotein. In some embodiments, the detection agent comprises a detectable label. In some embodiments, the detection agent comprises an antibody or an antigen-binding antibody fragment. In some embodiments, the kit further comprises a reagent, a buffer, an apolipoprotein standard, and/or a substrate useful in an ELISA assay. In some embodiments, the kit further comprises a reagent useful for dissociating a lipoprotein particle.

The above summary is meant to illustrate certain embodiments of the current disclosure, and is thus descriptive and not limiting. Other embodiments, advantages, features, and uses of the invention will be apparent to the skilled artisan from the detailed description of certain non-limiting embodiments, the drawings, and the claims.

DETAILED DESCRIPTION OF CERTAIN EXEMPLARY EMBODIMENTS

Figure 1:
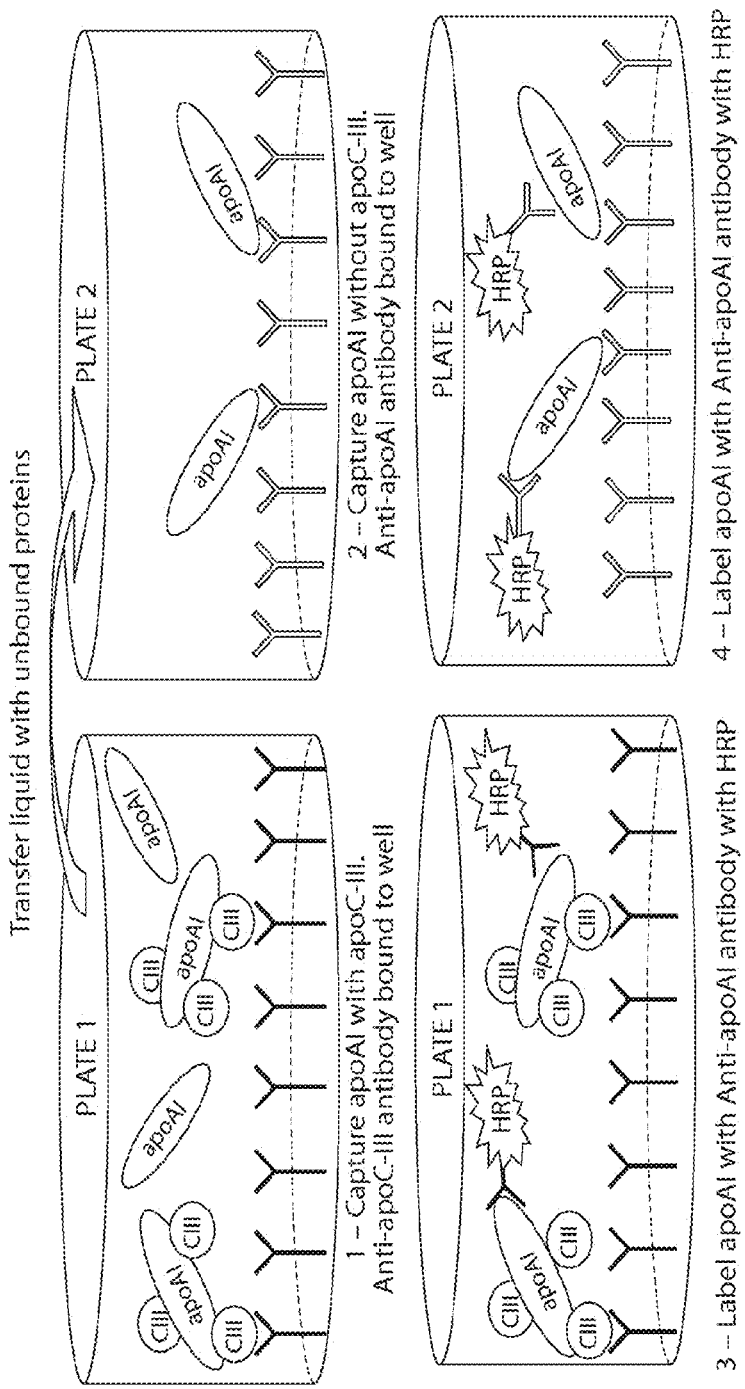
FIG. 1. Illustration of Protocol I.

Lipoproteins are lipid-protein particles that facilitate the transport of lipids and other hydrophobic compounds in the aqueous circulation. Lipoprotein particles comprise one of two mutually exclusive integral apolipoproteins: apolipoprotein (apo)A-I or apoB. Lipoprotein particles may also contain a variety of non-integral apolipoproteins, including, but not limited to, apoA-II, apoC-I, apoC-II, apoC-III, and apoE. While lipoproteins are essential for the transport of hydrophobic compounds, certain types of lipoprotein particles contribute to disease and/or disease risk, for example, to cardiovascular disease. Some aspects of this invention are based on the recognition that particles comprising certain combinations of integral and non-integral apolipoproteins and/or other components contribute to disease and disease risk, while particles comprising other combinations do not. Accordingly, the characterization of lipoproteins by the combination of integral and non-integral apolipoprotein content is increasingly important as research elucidates the effects of these apolipoproteins on lipoprotein metabolism and risk of disease, for example, cardiovascular disease.

The current method for quantifying lipids and lipoproteins with and without non-integral apolipoproteins is both time-consuming and expensive. Current protocols typically involve fractionation of lipoproteins in a biological sample into those containing and those deficient of the non-integral apolipoprotein of interest using immuno-affinity chromatography. For fractionation, biological samples, e.g., plasma samples obtained from a subject, are incubated overnight at 4° C. with Sepharose resin beads coated with antibody specifically binding the non-integral apolipoprotein of interest. The unbound fraction is eluted the next day with multiple column volumes of phosphate-buffered saline, followed by elution of the bound fraction using multiple column volumes of harsh ionic solutions. Elution with multiple column volumes results in a final sample many times diluted from plasma concentrations, requiring concentration of sample for the measurement of certain analytes.

The ionic solutions used to release the bound lipoproteins can also interfere with subsequent measurement assays and must be removed from the fraction prior to analysis. Following fractionation, lipoprotein concentration is measured by standard sandwich ELISA while lipid concentration is measured by enzymatic assays. The time and cost of this type of immuno-affinity/ELISA assay is prohibitive for use in large epidemiological cohorts or as a clinical diagnostic.

The term analyte refers to a molecule the presence or absence or the quantity of which is subject to analysis. In the context of lipoproteins, an analyte is typically a molecule comprised in a lipoprotein particle, for example, a protein or peptide (e.g., an integral or non-integral apolipoprotein), a lipid (e.g., a triacylglycerol, a cholesterol, or cholesterol derivative), or any other molecule or molecule type known to be comprised in or otherwise associated with lipoprotein particles. An analyte typically is a molecule, the detection or quantification of which is of interest to a researcher or clinician, for example, for research or diagnostic purposes. An analyte may be a biomarker, for example, a biomarker the presence, absence, or quantity of which in a sample indicates a particular condition of the sample or the subject, experiment, or environment that the sample was obtained from. In some embodiments, an analyte is a biomedical biomarker, for example, a protein or peptide in a sample obtained from a subject diagnosed with or suspected to have a disease or condition, wherein the presence, absence, or quantity of the biomarker in the sample is indicative of the presence, absence, or state of the disease or condition in the subject. For example, in some embodiments, a diagnostic assay provided herein comprises the detection of a molecule comprised in a lipoprotein particle, the presence, absence, or quantity of which in a blood or serum sample obtained from a subject is indicative of the presence, absence, or state of a disease, such as cardiovascular disease in the subject, or of the subject being at an elevated risk of developing a disease, for example, cardiovascular disease, as compared to a control subject. e.g., as compared to an average subject or as compared to an age-matched and sex-matched healthy subject.

The term antibody refers to an immunoglobulin, whether natural or wholly or partially synthetically produced. Antibody derivatives which maintain specific binding ability, for example, antigen-binding antibody fragments, such as Fab, Fab', or F(ab')$_2$ fragments, or engineered antibodies, such as scFvs, are also included referred to by the term antibody. The term also refers to any protein having a binding domain which is homologous or largely homologous to an immunoglobulin binding domain. These proteins may be derived from natural sources, or partly or wholly synthetically produced. An antibody may be monoclonal or polyclonal. An antibody may be a member of any immunoglobulin class, including, but not limited to, any of the human classes: IgG, IgM, IgA, IgD, and IgE.

The term antibody fragment refers to any derivative of an antibody that is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv, diabody, single variable domain, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains that are linked together, for instance, by disulfide linkages. The fragment may also optionally be a multi-molecular complex. A functional antibody fragment will typically comprise at least about 50 amino acids and more typically will comprise at least about 200 amino acids. Single-chain Fvs (scFvs) are recombinant antibody fragments consisting of only the variable light chain ($V_L$) and variable heavy chain (VH) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. Diabodies are dimeric scFvs. The components of diabodies typically have shorter peptide linkers than most scFvs, and they show a preference for associating as dimers. An Fv fragment is an antibody fragment which consists of one $V_H$ and one $V_L$ domain held together by non-covalent interactions. The term dsFv is used herein to refer to an Fv with an engineered intermolecular disulfide bond to stabilize the $V_H$-$V_L$ pair. An F(ab')$_2$ fragment is an antibody fragment essentially equivalent to that obtained from immunoglobulins (typically IgG) by digestion with an enzyme pepsin at pH 4.0-4.5. The fragment may be recombinantly produced. A Fab' fragment is an antibody fragment essentially equivalent to that obtained by reduction of the disulfide bridge or bridges joining the two heavy chain pieces in the F(ab')$_2$ fragment. The Fab' fragment may be recombinantly produced. A Fab fragment is an antibody fragment essentially equivalent to that obtained by digestion of immunoglobulins (typically IgG) with the enzyme papain. The heavy chain segment of the Fab fragment is the Fd piece.

The term apolipoprotein refers to a protein that binds a lipid (e.g., triacylglycerol or cholesterol) to form a lipoprotein. Apolipoproteins also serve as enzyme cofactors, receptor ligands, and lipid transfer carriers that regulate the metabolism of lipoproteins and their uptake in tissues. There are two major types of apolipoproteins: integral and non-integral apolipoproteins. Lipoproteins comprise one of two mutually exclusive integral apolipoproteins—apoA-I in high-density lipoproteins, and apoB in very-low density lipoproteins (VLDL), intermediate density lipoproteins (IDL), low-density lipoproteins (LDL), and lipoprotein(a). Lipoproteins may also comprise one or more non-integral apolipoproteins. There are several categories of apolipoproteins and several sub-classes including: apoA (e.g., apo A-I, apo A-II, apo A-IV, and apo A-V); B (e.g., apo B48 and apo B100); apoC (e.g., apo C-I, apo C-II, apo C-III, and apo C-IV); apoD; apoE; apoH, and apoJ. Additional apolipoproteins are described in Table 2, and further apolipoproteins are known to the skilled artisan. The disclosure is not limited in this respect.

The term binding agent refers to a molecule that binds to another molecule with high affinity. In some embodiments, the binding is through non-covalent interaction. In some embodiments, the binding is specific, meaning that the binding agent binds only one particular type of molecule, or a narrow class of highly similar molecules with high affinity. For example, in some embodiments, a binding agent specifically binding apoC-III is a binding agent that binds apoC-III with high affinity and does not bind, or binds only with low affinity to other molecules, including other proteins (e.g., other apolipoproteins). Non-limiting examples of binding agents are antibodies, antibody fragments, aptamers, and adnectins.

The term conjugated refers to a state of relatively stable association between two entities, for example, between a binding agent, such as an antibody, and a solid support, for example, an ELISA plate well surface. In some embodiments, conjugated entities are linked by a direct or indirect covalent or non-covalent interaction. Non-covalent interactions that result in conjugation include, but are not limited to hydrogen bonding, van der Waals interactions, hydrophobic interactions, magnetic interactions, and electrostatic interactions. Typically, two conjugated entities are associated with each other in a manner stable enough to withstand the conditions typically encountered during a detection assay as described herein or otherwise suitable for application according to aspects of this disclosure. For example, in embodiments, where an ELISA is performed a binding agent is associated to an ELISA plate well surface in a manner sufficient for the bond between the two to endure the binding and washing steps typically comprised in the ELISA method used.

The term depleting of in the context of contacting a sample with a binding agent binding a molecule comprised in the sample, refers to a diminishment of the abundance of the molecule in the sample. For example, if the binding agent is admixed with the sample, incubated under conditions that allow the binding agent to bind the molecule, and the binding agent (and any molecule bound thereto) are separated from the sample, for example, by removing the sample from a solid support the binding agent is conjugated to, the sample will be depleted of the bound molecule. The depletion of the molecule may be complete, resulting in no molecule of the kind bound by the binding agent remaining in the sample, or partial, resulting in a reduction of the abundance of the molecules bound by the binding agent in the sample. Accordingly, a sample depleted of a molecule may be a sample free of that molecule, or a sample in which the abundance of that molecule has been reduced, for example, by contacting the sample with a binding agent binding the molecule, and by removal of the binding agent (with bound molecule) from the sample. The depletion will be more complete in embodiments, where a high-affinity binding agent is used, for example, an antibody, and where the binding agent is in excess of the target molecule.

The term detectable label refers to a molecule or moiety that can be detected, for example, by performing an assay known to those of skill in the art for its detection. A detectable label, accordingly, may be, for example, (i) an isotopic label (e.g., a radioactive or heavy isotope, including, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$), (ii) an affinity label (e.g., an antibody or antibody fragment, an epitope, a ligand or a ligand-binding agent) (iii) and enzymatic label that produce detectable agents when contacted with a substrate (e.g., a horseradish peroxidase or a luciferase); (iv) a dye, (e.g., a colored, luminescent, phosphorescent, or fluorescent molecule, such as a chemical compound or protein). Fluorophores, for example, fluorescent dyes and proteins, are of particular use for embodiments of this invention that involve detection via flow cytometry or on a chip surface. A fluorophore is a molecule or moiety that absorbs light of a specific wavelength and then re-emits light at a different specific wavelength, thus causing the molecule of moiety to be fluorescent. Other suitable detectable labels are known to those of skill in the art and the invention is not limited in this respect.

The term detection agent refers to an agent that can be detected. Typically, a detection agent comprises a binding agent that specifically binds a target molecule, for example, an apolipoprotein, and a detectable label. The binding agent can be conjugated to the detectable label by any method known to those of skill in the art. Conjugation of binding agent and detectable label can be effected before or after a sample is contacted with the binding agent. In embodiments, where an ELISA detection step is performed, exemplary useful detection agents include, but are not limited to, antibodies and antibody fragments that are conjugated to an enzyme catalyzing a reaction producing an ELISA-appropriate emission of light, for example, a horseradish peroxidase or a luciferase. Exemplary detection agents are provided herein and additional detection agents will be apparent to those of skill in the art. The disclosure is not limited in this respect.

The terms dissociating and fractionating, as used herein in the context of lipoprotein particles, refers to a breaking up of non-covalent interactions contributing to the structural integrity of lipoprotein particles, thus resulting in the freeing of components, e.g., proteins, lipids, and cholesterol or cholesterol derivatives comprised in lipoprotein particles. In some embodiments, dissociating or fractionating of lipoprotein particles is achieved by contacting them with a detergent, for example, with TWEEN 20™.

The terms lipoprotein and lipoprotein particle refer to particles comprising both proteins and lipids. Typically, lipoprotein particles comprise a phospholipid monolayer around a hydrophobic core comprising lipids (e.g., triacylglycerols, cholesterol, and other hydrophobic compounds), as well as integral and non-integral apolipoproteins. Lipoprotein particles represent an important vehicle for transporting hydrophobic substances in the aqueous circulation of the body. Lipoprotein particles comprise one of two mutually exclusive integral apolipoproteins, apolipoprotein apoA-I or apoB, and may also comprise one or more non-integral apolipoproteins, including, but not limited to, apoA-II, apoC-I, apoC-II, apoC-III, and apoE. Lipoprotein particles can be classified based on their density into five classes: chylomicrons (ChM), very low density lipoprotein (VLDL), intermediate density lipoproteins (IDL), low density lipoproteins (LDL) and high density lipoproteins (HDL). A non-limiting overview of some exemplary characteristics of the different classes of lipoproteins is given in Table 1 below:

TABLE 1

| lipoprotein classification by density | | | | | | |
|---|---|---|---|---|---|---|
| Density (g/ml) | Class | Diameter (nm) | protein | cholesterol | phospholipid | triacylglycerol |
| >1.063 | HDL | 5-15 | ~33% | ~30% | ~29% | ~4% |
| 1.019-1.063 | LDL | 18-28 | ~25% | ~50% | ~21% | ~8% |
| 1.006-1.019 | IDL | 25-50 | ~18% | ~29% | ~22% | ~31% |

TABLE 1-continued lipoprotein classification by density

| Density (g/ml) | Class | Diameter (nm) | protein | cholesterol | phospholipid | triacylglycerol |
|---|---|---|---|---|---|---|
| 0.95-1.006 | VLDL | 30-80 | ~10% | ~22% | ~18% | ~50% |
| <0.95 | ChM | 100-1000 | <2% | ~8% | ~7% | ~84% |

The term plurality, as used herein, refers to two or more of the elements so qualified.

The term sample refers to a composition of matter representative of a biological, clinical, or experimental environment. For example, a biological sample may be a sample obtained from a subject, such as a body fluid sample, or a cell or tissue sample, or a sample obtained from an experimental environment, such as a composition comprising a small molecule compound, a cell culture supernatant, a composition comprising an engineered organ, and so forth. Non-limiting examples of samples are a serum sample, a blood sample, a plasma sample, a urine sample, and a tissue sample. In some embodiments, a sample is a biological sample. In some embodiments, a sample is a tissue or body fluid sample obtained from a subject.

The term body fluid refers to any body fluid including, without limitation, blood, serum, plasma, lymph fluid, synovial fluid, follicular fluid, seminal fluid, amniotic fluid, whole blood, sweat, urine, cerebrospinal fluid, saliva, semen, sputum, tears, perspiration, mucus, tissue culture medium, tissue extracts, and cellular extracts. It may also apply to fractions and dilutions of body fluids. The source of a body fluid can be a human body, an animal body, such as the body of an experimental animal.

The term subject refers to a human, a non-human primate, a non-human mammal (e.g., a cow, a horse, a pig, a sheep, a goat, a dog, a cat, or a rodent), or a vertebrate. In some embodiments, a subject is a laboratory animal (e.g., a mouse, rat, cat, dog, pig, cow, hamster, gerbil, or a frog). In some embodiments, for example, in some embodiments involving a clinical application of an aspect of this invention, the subject is diagnosed with or suspected to have a disease or condition.

The term triacylglycerol (TAG) is used herein interchangeably with the terms triglyceride, and triacylglyceride, and refers to a molecule comprising three fatty acid molecules covalently bound to a glycerol molecule via ester bonds.

Methods and Reagents for Lipoprotein Detection and Quantification

Figure 5:
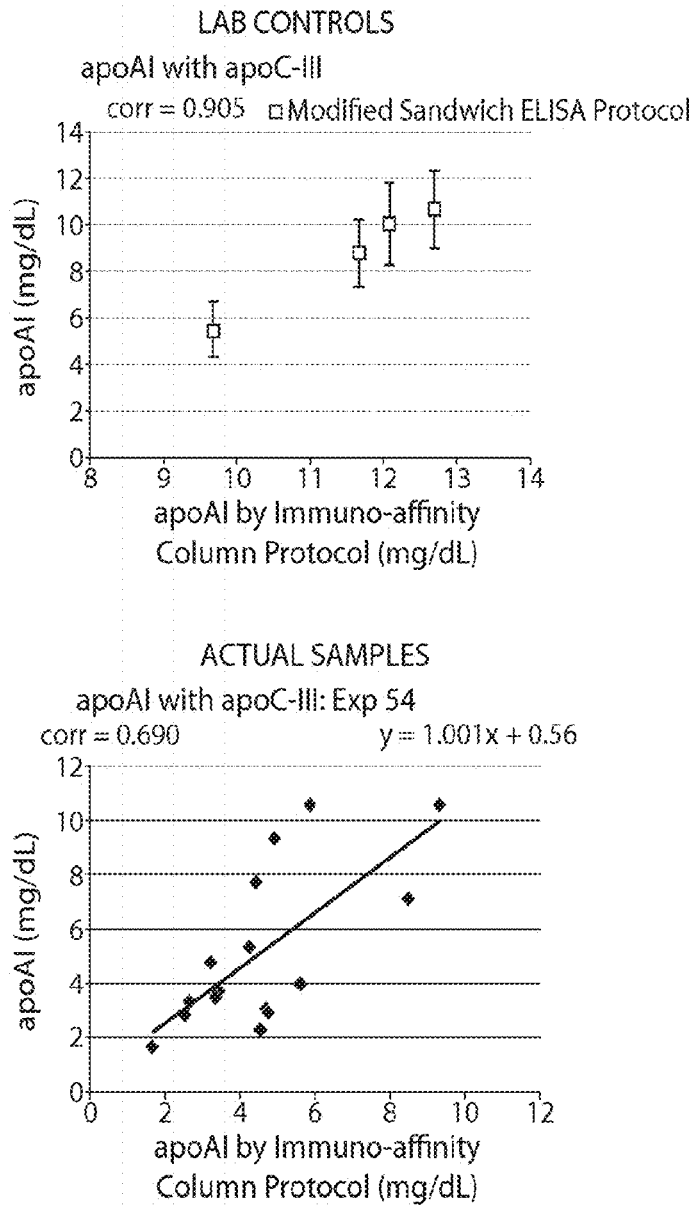
FIG. 5. Comparison of apoC-III with ApoA-I measured with the technology described herein and with an immuno-affinity method.

Some aspects of this disclosure provide a new technology to quantify the concentration of lipids and lipoproteins with and without a non-integral apolipoprotein of interest utilizing a modified sandwich ELISA protocol that is easier, faster, and less expensive than the current standard method. The technology described herein obviates the time-consuming and costly immuno-affinity fractionation comprised in current methods for quantitation of lipoprotein particles based on their apolipoprotein content. Correlation studies of data obtained from the technology provided herein compared to the "gold standard" current immuno-affinity method for the detection of lipoprotein particles comprising apoA-I or apoB, either with or without apoC-III using 82 to 86 samples yielded within-batch correlation coefficients within the range of 0.838 to 0.996 and actual concentration values were within the expected range of each other. In more recent sets of data, the slope of the line plotting concentrations of apoA-I with apoC-III in the same sample as determined by both the "gold-standard" protocol and our new protocol is 1.001, suggesting a high degree of accuracy (FIG. 5).

The technology described herein can be further extended to the analysis of any analyte of interest comprised in lipoproteins. The technology described herein can be used to analyze any number of analytes of interest in lipoprotein particles. For example, the technology provided herein can be used to quantify the amount of lipoproteins in a biological sample that comprise a specific combination of integral and non-integral apolipoproteins. e.g., the amount of particles comprising apoA-I, the amount of particles comprising apoB, the amount of particles comprising apoA-I and apoC-III, the amount of particles comprising apoA-I, apoC-III, and apoE, and so forth.

In some embodiments, a biological sample is contacted with a binding agent binding an analyte of interest, for example, an antibody specifically binding a non-integral apolipoprotein. In some embodiments, the binding agent is conjugated to a solid support, e.g., a stationary phase, such as the surface of an ELISA plate well. Any bound lipoprotein particles are thus immobilized on the solid support, and unbound lipoproteins, which do not comprise the analyte of interest, e.g., the non-integral apolipoprotein of interest, remain in solution and can be removed for quantification or further processing. In some embodiments, a level of a specific lipoprotein particle type (e.g., of lipoprotein particles comprising apoA-I and apoC-III, or of particles comprising apoE but no apoC-III, and so forth) is used as a biomarker indicative of a disease or of an elevated risk to develop a disease, e.g., cardiovascular disease. In some embodiments, a ratio of lipoprotein particles comprising the analyte to lipoprotein particles not comprising the analyte is calculated, for example, a ratio of lipoprotein particles comprising apoA-I and apoC-III to lipoprotein particles comprising apoA-I but devoid of apoC-III. In some embodiments, such a ratio is used as a biomarker indicative of a disease or of an elevated risk to develop a disease, e.g., cardiovascular disease.

The technology provided herein allows for the analysis and quantification of any number of different analytes, e.g., apolipoproteins, lipids, or other components of lipoproteins, whose concentration in lipoproteins may be of interest. Such analytes can include for example, and without limitation, integral apolipoproteins (apoA-I and apoB), any of the non-integral apolipoproteins, phospholipids, other lipids that have been modified by oxidation or other enzymatic reactions occurring in the body (e.g., oxidized cholesterol and triacylglycerol), and any other analyte of interest that can be bound by a binding agent such as an antibody. In some embodiments, the content of various lipids such as cholesterol or triglyceride can be measured in lipoproteins of interest such as, for example, HDL that has apoC-III or apoE. Exemplary analytes for which antibodies compatible with the technology described herein and which may be detected in or on lipoprotein complexes are provided in Table 2 together with a listing of exemplary, commercially available antibodies that are suitable for use in some embodiments of the technology described herein.

TABLE 2

| Protein ID | Protein Name | SOURCE | CATALOG# |
|---|---|---|---|
| IPI00021841 | apoA-I | US Biological | A2299-07F |
| IPI00021854 | apoA-II | US Biological | A2299-32M |
| IPI00304273 | apoA-IV | US Biological | A2299-36D |
| IPI00021842 | apoE | US Biological | A2299-75H |
| IPI00021855 | apoC-I | US Biological | A2299-61P |
| IPI00021856 | apoC-II | US Biological | A2299-65P |
| IPI00021857 | apoC-III | US Biological | A2299-68R |
| IPI00022731 | apoC-IV | US Biological | A2299-72M |
| IPI00177869 | apoL-I | US Biological | A2299-11C |
| IPI00030739 | apoM | US Biological | A2299-42C |
| IPI00299435 | apoF | US Biological | A2299-76V1 |
| IPI00006662 | apoD | US Biological | A2299-72G |
| IPI00298828 | apoH | US Biological | A2299-77F |
| IPI00291262 | Clusterin (apoJ) | US Biological | C5870-01M |
| IPI00022331 | LCAT (phosphatidylcholine-sterol acyltransferase) | US Biological | L1662-50 |
| IPI00006173 | CETP | US Biological | C3050-03A |
| IPI00022733 | PL transfer protein | US Biological | P4278-02 |
| IPI00452748 | SAA1 | US Biological | S1002-50A |
| IPI00006146 | SAA2 | NovUS Biological | H00006289-D01P |
| IPI00019399 | SAA4 | US Biological | S1002-60A |
| IPI00218732 | PON 1 | US Biological | P3107-76B |
| IPI00299778 | PON 3 | US Biological | P3107-80A |
| IPI00164623 | Complement C3 | US Biological | C7850-12L |
| IPI00020091 | α-1-acid glycoprotein 2 | US Biological | A0550-40C |
| IPI00022431 | α-2-HS-glycoprotein | US Biological | A8509-50A |
| IPI00305457 | α-1-antitrypsin | US Biological | A2298-29G |
| IPI00022895 | α-1B-glycoprotein | US Biological | A0905-01A |
| IPI00021885 | Fibrinogen (alpha-chain) | US Biological | F4203-06Q |
| IPI00022463 | Serotransferrin | US Biological | S1001-75 |
| IPI00296170 | Haptoglobin-related protein | Millipore | ABS196 |
| IPI00022432 | Transthyretin | US Biological | P6000-02H |
| IPI00298853 | Vitamin D-binding protein | US Biological | V2130-16 |
| IPI00022229 | apoB-100 | US Biological | A2298-90B |
| IPI00022434 | Serum albumin | US Biological | A1274-88A |
| IPI00418163 | Complement C4B | US Biological | C7850-17J |
| IPI00032258 | Complement C4A | US Biological | C7850-16L |
| IPI00022395 | Complement C9 | US Biological | C7850-52 |
| IPI00298971 | Vitronectin | US Biological | V2202D |
| IPI00029863 | α-2-antiplasmin | US Biological | A2298-13R |
| IPI00022426 | α-1-microglobulin/bikunin | US Biological | M3890-11A |
| IPI00218192 | Inter-a-trypsin inhibitor H4 | Santa Cruz Biotechnology | sc-34471 |
| IPI00032220 | Angiotensinogen | US Biological | A2294-48P |
| IPI00006114 | Serpin peptidase inhibitor | antibodies-online.com | ABIN457963 |
| IPI00032328 | Kininogen-1 | Abcam | ab97761 |
| IPI00022420 | Plasma retinol-binding protein | US Biological | R1701-35M1 |
| IPI00337558 | Prenylcysteine oxidase | US Biological | P6201-35A |
| IPI00022488 | Hemopexin | US Biological | H1865-10 |
| | α-1-acid glycoprotein 1 | US Biological | A0550-04A |
| | Gelsolin | US Biological | G2024-53K |
| | zinc a-2 glycoprotein | US Biological | Z0133-01 |
| | hemoglobin subunit beta | Abcam | ab100952 |
| | pigment epithelium derived factor | US Biological | P4350-15F |
| | α-1-antichymotrypsin | US Biological | A2298-01L |
| | heparin cofactor 2 | US Biological | H1892-51 |
| | antithrombin III | US Biological | A2298-17F |
| | complement B | Novus Biologicals | NB120-8840 |
| | Prothrombin | US Biological | P9115 |
| | aminopeptidase N | Aviva Systems Biology | ARP61079_P050 |
| | hemoglobin subunit alpha | US Biological | H1850-13H |
| | catheliciden antimicrobial peptide | Novus Biologicals | NBP1-30755 |
| | leucine-rich a-2 glycoprotein | US Biological | L2020-67 |
| | phosphatidylinositol-glycan-specific phospholipase D | US Biological | G8583 |
| | Inter-a-trypsin inhibitor H2 | Santa Cruz Biotechnology | sc-21975 |
| | band 3 anion transport protein | US Biological | S5329-04A |
| | carbonic anhydrase 1 | US Biological | C1105-05H |
| | N-acetylmuramoyl-L-alanine amidase | US Biological | P3292-04 |
| | β-2-microglobulin | US Biological | M3890H |
| | filamin-A | US Biological | F4510-79K |
| | Fibronectin | US Biological | F4215-05 |
| | integrin a-II-b | US Biological | I7661-32C |
| | thrombospondin I | US Biological | T5100-06R |
| | complement C1s subcomponent | US Biological | C7850-08J |

TABLE 2-continued

| Protein ID | Protein Name | SOURCE | CATALOG# |
|---|---|---|---|
| | Lumican | US Biological | L6025 |
| | Afamin | US Biological | A0922-01 |
| | Lipoprotein Associated Phospholipase A2 (PAF-AH) | US Biological | L2640-11B |
| | hemoglobin binding protein | | |
| | apo (a) | US Biological | A2299-80 |
| | apoB | US Biological | A2298-90B |
| | platelet basic protein | US Biological | N0023-01G |

Analyte names are official IPI/UniProt/GenBank abbreviations or names. IPI identifiers are exemplary, non-limiting, and for illustration purposes only. IPI identifiers are according to the final release of the International Protein Index of Sep. 27, 2011, available at the European Bioinformatics Institute.

The above list of analytes that can be detected and/or quantified in or on lipoprotein particles according to aspects of this disclosure and of suitable antibodies that can be used in connection with the technology described herein is not limiting, and many additional analytes and suitable binding agents, including additional commercially available antibodies and antibody fragments, will be apparent to those of skill in the art. Some exemplary analytes and binding agents are described in Vaisar et al., *Shotgun proteomics implicates protease inhibition and complement activation in the anti-inflammatory properties of HDL*. J Clin Invest. 2007; 117 (3):746 doi: 10.1172/JCI26206; Alwaili et al., *The HDL proteome in acute coronary syndromes shifts to an inflammatory profile*. Biochim Biophys Acta. 2012 March; 1821 (3):405-15. Epub 2011 Jul. 23; Davidson et al., *Proteomic analysis of defined HDL subpopulations reveals particle-specific protein clusters: relevance to antioxidative function*. Arterioscler Thromb Vasc Biol. 2009 June; 29(6):870-6. Epub 2009 Mar. 26; and Asztalos et al., *Metabolic and functional relevance of HDL subspecies*. Current Opinion in Lipidology 2011; 22(3): 176-185: the entire contents of each of which are incorporated herein by reference.

For example, the technology described herein allows for the detection and/or quantification of lipoprotein particles in a biological sample that comprise apoA-I; apoA-I and apoC-III; apoA-I and no apoC-III; apoA-I and apoE; apoA-I, apoC-III, and apoE; apoE and no apoC-III; apoA-II and apoL; apoB and apoC-III; apoB, apoA-II, and apoC-IV; apoA-I and Clusterin; apoB, apoD, and LCAT, and so on. The technology described herein allows for the detection and/or quantification of lipoprotein particles in a biological sample that comprise any single analyte, or any combination of two or more analytes of interest, for example, of the analytes described in Table 2. Many additional combinations of analytes suitable for detection and/or quantification in or on lipoprotein particles according to aspects of this disclosure will be apparent to the skilled artisan based on this disclosure.

Protocol I

In some embodiments, a method for detection and/or quantification of lipoprotein particles in a biological sample is provided herein that allows for the direct detection and/or quantification of lipoprotein particles comprising an analyte or a combination of analytes of interest after the lipoprotein particles are bound to a solid support by a binding agent specifically binding the analyte of interest. An exemplary embodiment of such a method is illustrated in FIG. 1. In some embodiments, the biological sample is contacted with a binding agent specifically binding the analyte of interest, for example, a non-integral apolipoprotein. In some embodiments, the binding agent is conjugated to a solid support, thus immobilizing the bound lipoprotein particles. After unbound lipoprotein particles, which do not comprise the analyte of interest, are removed, the bound lipoprotein particles can be contacted with a second binding agent to detect a second analyte of interest (e.g., a second apolipoprotein). Any bound second binding agent can then be detected or quantified, e.g., using a secondary antibody conjugated to a detection agent, such as a fluorescent moiety or an enzyme useful in an ELISA method.

For example, in some embodiments, a biological sample is contacted with an antibody specifically binding apoC-III. In some embodiments, the antibody is conjugated to the surface of an ELISA plate well, and the contacting is achieved by transferring the biological sample to the well. The sample is then incubated under conditions and for a time period suitable for the antibody to bind apoC-III comprised in lipoprotein particles, thus immobilizing any lipoprotein particles comprising apoC-III in the sample to the ELISA plate well surface. In some embodiments, the sample, including any unbound lipoprotein particles that do not comprise apoC-III, is then removed from the well. The bound, apoC-III comprising lipoprotein particles can then be contacted with a binding agent specifically binding a second analyte. e.g., with an antibody against apoA-I. After washing away any unbound binding agent, the second binding agent bound to the immobilized apoC-III lipoprotein particles can be detected and/or quantified, for example, with a secondary antibody and an ELISA which can be performed directly on the plate well used to immobilize the lipoprotein particles. In this exemplary embodiment, the detection of apoA-I in the bound lipoprotein particles would indicate the presence and/or abundance of lipoprotein particles comprising apoA-I and apoC-III. A ratio of these lipoprotein particles to other lipoprotein particles (e.g., lipoprotein particles comprising apoA-I but no apoC-III) can be calculated based on a detection/quantification of lipoprotein particles in the sample, e.g., after the sample is removed from the ELISA well comprising the apoC-III antibody (see FIG. 1).

In some embodiments, the method comprises contacting a sample comprising lipoprotein particles with a binding agent that specifically binds a non-integral apolipoprotein. In some embodiments, the binding agent binds to the non-integral apolipoprotein, and, thus, the sample is depleted of the bound apolipoprotein. In some embodiments, the contacting is performed under conditions that do not disturb lipoprotein particle integrity, thus the binding of the apolipoprotein to the binding agent depletes the sample of lipoprotein particles comprising the bound apolipoprotein. In some embodiments, the method further comprises removing the sample, now depleted of lipoprotein particles comprising the non-integral apolipoprotein, from the binding agent. This can be achieved by any method for separation of binding agent from a sample known in the art. For example, the binding agent may be conjugated to a solid support, e.g., the surface of an ELISA plate well, or a resin or bead surface, and can be removed from the liquid phase of the sample by physically separating the solid support from the liquid phase, for example, by pipetting or by magnetic separation (e.g., using MACS beads conjugated to the binding agent). In some embodiments, the depleted sample is contacted with a binding agent that specifically binds an integral apolipoprotein (e.g., apoA-I or apoB). In some embodiments, the sample is then removed from the binding agent binding the integral apolipoprotein. In some embodiments, the method comprises detecting an integral apolipoprotein (e.g., apoA-I or apoB) bound to the binding agent binding the non-integral apolipoprotein and/or bound to the binding agent binding the integral apolipoprotein.

Because the binding is performed in some embodiments under conditions leaving the structural integrity of the lipoprotein particles intact, the direct binding of the binding agents to the respective integral or non-integral apolipoprotein will result in the immobilization of lipoprotein particles comprising the respective component on the binding agent, or, as it may be, any solid support that the binding agent is conjugated to. For example, if each binding agent is conjugated to the surface of an ELISA plate well, the well comprising the binding agent binding the non-integral apolipoprotein will comprise immobilized lipoprotein particles containing the non-integral apolipoprotein, and the well comprising the binding agent binding the integral apolipoprotein will comprise immobilized lipoprotein particles containing the integral apolipoprotein. The detection of integral apolipoprotein in both populations of immobilized lipoprotein particles is used in some embodiments, to quantify the abundance of the respective lipoprotein particles (e.g., particles comprising apoC-III and particles comprising apoA-I but no apoC-III in the example above).

Accordingly, in some embodiments, the method described allows for the isolation, detection, and quantification of lipoprotein particles comprising a specific non-integral apolipoprotein and/or integral apolipoprotein combination. In some embodiments, the sample is sequentially contacted with different binding agents, each of which binding a different non-integral apolipoprotein. For example, in some embodiments, a sample if first contacted with a binding agent binding apoC-III, then with a binding agent binding apoE, and finally with a binding agent binding apoA-I. The resulting populations of lipoprotein particles in this example are lipoprotein particles comprising apoC-III; lipoprotein particles comprising apoE, but not apoC-III; and lipoprotein particles comprising apoA-I, but neither apoC-III nor apoE. In some embodiments, the sample is contacted with 2, 3, 4, 5, 6, 7, 8, 9, 10, 11, 12, 13, 14, 15, 16, 17, 18, 19, 20, or more than 20 different binding agents, each binding a different analyte of interest comprised in lipoprotein particles, for example, each binding a different non-integral or integral apolipoprotein.

Because all lipoprotein particles comprise an integral apolipoprotein, detecting an integral apolipoprotein can be used to quantify each population of lipoprotein particles. In some embodiments, a detection agent that binds one of the two integral apolipoproteins (e.g., apoA-I or apoB) is used, resulting in the quantification of only the lipoprotein particle population comprising the respective integral apolipoprotein. In other embodiments, a detection agent is used that detects both integral apolipoproteins, or a molecule comprised in all lipoprotein particles, for example, a detection agent that non-specifically detects phospholipids comprised in lipoprotein particles. Such a detection strategy allows the quantification of a lipoprotein particle population comprising a specific non-integral apolipoprotein or other analyte of interest that is not limited to a population of lipoprotein particles comprising a single integral apolipoprotein. In other words, using a detection agent binding apoA-I or apoB allows for a quantification of lipoprotein particle subtypes in the HDL or VLDL and LDL lipoprotein particle populations, respectively, while using a detection agent binding both apoA-I or apoB allows for a quantification of lipoprotein particle subtypes in the composite (HDL and VLDL and LDL) lipoprotein particle population in the sample.

In some embodiments, the detection agent is the same for all lipoprotein particle populations analyzed. In other embodiments, each subpopulation is subjected to a detection using a different detection agent, for example, a detection agent binding the same lipoprotein particle component as the binding agent used to isolate the lipoprotein particles from the sample. For example, in some embodiments, an apoC-III-containing lipoprotein particle population is first removed from a sample, and then an apoA-I-containing lipoprotein particle population is subsequently removed from the sample. In some embodiments, the detection and/or quantification of both populations is performed with the same detection agent, e.g., a detection agent binding apoA-I as illustrated in FIG. 1. In some embodiments, however, the lipoprotein particle population comprising apoC-III lipoprotein particles may be detected by using an apoC-III-binding detection agent. Alternatively, in some embodiments, a detection agent is used that binds to a different analyte (e.g., a different apolipoprotein, such as apoE, apoF, etc.), or to a molecule comprised in all lipoprotein particles, such as a specific phospholipid.

In some embodiments, the method comprises quantifying a lipoprotein particle population comprising a specific analyte. In some embodiments, the method comprises quantifying a plurality of lipoprotein particle populations and calculating a ratio between two or more lipoprotein particle populations. For example, in some embodiments, a ratio may be calculated of the abundance of lipoprotein particles comprising apoC-III to the abundance of lipoprotein particles comprising apoA-I but not apoC-III in a sample, or of the abundance of lipoprotein particles comprising apoC-III to the abundance of lipoprotein particles comprising apoE in a sample, and so forth. Such ratios are useful as biomarkers in the detection of normal and diseased states as well as in the detection of an elevated risk to develop a disease in a subject. Some examples of such biomarkers are known to those of skill in the art. For some exemplary biomarkers based on lipoprotein particle abundance and/or ratio, see, Jensen M et al., *Apolipoprotein C-III as a Potential Modulator of the Association Between HDL-Cholesterol and Incident Coronary Heart Disease* J Am Heart Assoc. 2012; 1:jah3-e000232; and Mendivil C et al., *Low-Density Lipoproteins Containing Apolipoprotein C-III and the Risk of Coronary Heart Disease*. Circulation. 2011 Nov. 8; 124(19): 2065-72; the entire contents of each of which are incorporated herein by reference.

Protocol II

Figure 3:
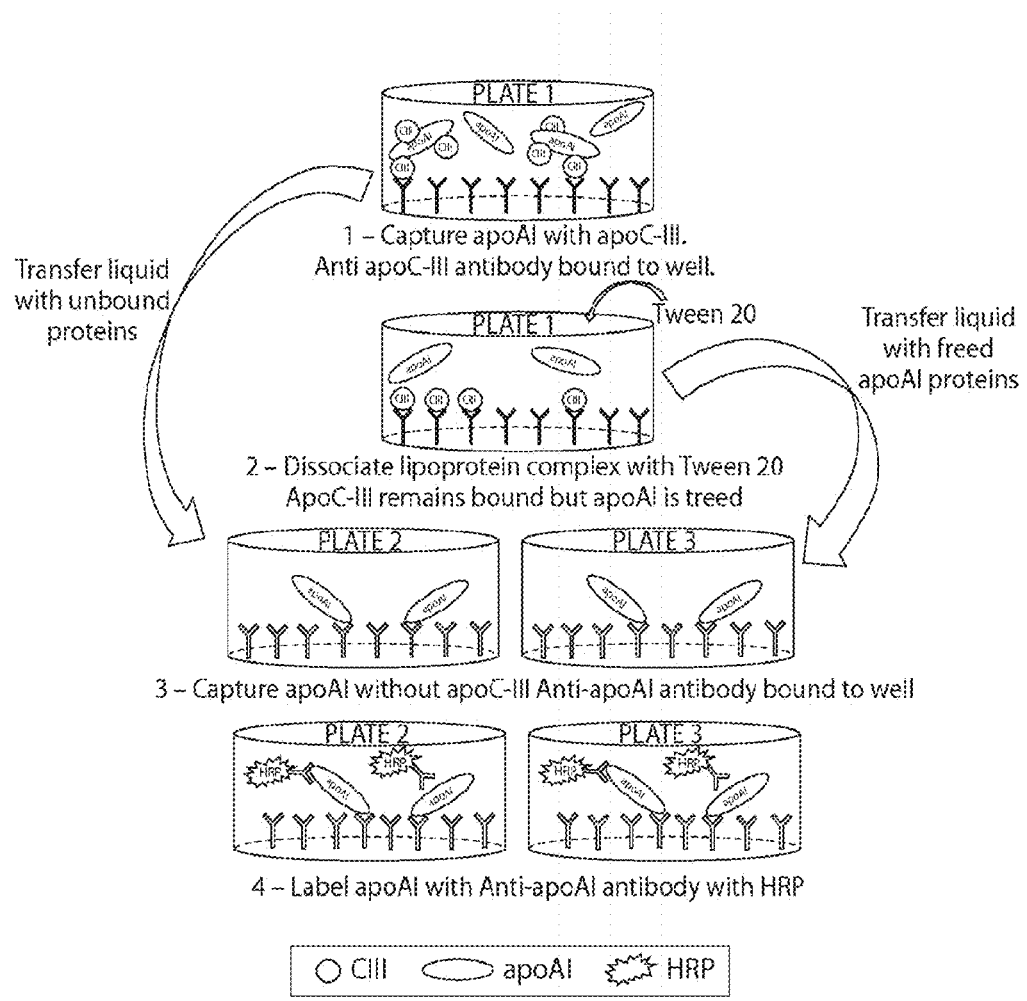
FIG. 3. Illustration of Protocol II.

In some embodiments, a method for detection and/or quantification of lipoprotein particles in a biological sample is provided, in which lipoprotein particles comprising an analyte of interest are immobilized on a solid support via a binding agent specifically binding the analyte, and the immobilized lipoprotein complexes are subsequently dissociated (e.g., via contacting them with a detergent), thus freeing the lipoprotein particle components not bound to the binding agent. The freed lipoprotein particle components can then be quantified. FIG. 3 comprises an illustration of an exemplary embodiment of this methodology. Lipoprotein particles not comprising the analyte and freed lipoprotein particle components can be detected and/or quantified using the same detection reagents and methodology. The fractionation of immobilized lipoprotein particles into free components allows for the parallel detection and/or quantification of any number of analytes in the fractionated sample.

In some embodiments, the method comprises contacting a sample with a binding agent that specifically binds a non-integral apolipoprotein, thereby depleting the sample of lipoprotein particles comprising the non-integral apolipoprotein. In some embodiments, the binding agent is conjugated to a solid support, for example, the surface of an ELISA plate well, thus allowing for the physical isolation of any bound lipoprotein particles (comprising the non-integral apolipoprotein) from the sample. In some embodiments, the bound lipoprotein particles are dissociated, for example, by contacting them with a detergent, such as TWEEN 20™, and the dissociated components of the lipoprotein particles are contacted with a binding agent that specifically binds an integral apolipoprotein. In some embodiments, the sample, depleted of the lipoprotein particles comprising the non-integral apolipoprotein used in the first contacting step above is removed from the binding agent, and the sample is subsequently contacted with a binding agent that specifically binds an integral apolipoprotein. The method further comprises a detection step similar to that in protocol I, except that in the case of dissociated components, the detection agent has to bind the same lipoprotein particle component as the binding agent.

For example, in some embodiments, the first binding agent binds apoC-III, and the lipoprotein particle population of the sample is depleted of lipoprotein particles comprising apoC-III, because lipoprotein particles binding apoC-III are bound to the binding agent (see FIG. 3). The remainder of the sample, comprising apolipoproteins and lipoproteins that do not bind the binding agent, is removed from the binding agent, and is contacted with a binding agent binding apoA-I. Any lipoprotein particles comprising apoA-I will bind to the second binding agent. In some embodiments, the apoC-III-comprising lipoprotein particles bound to the first binding agent are dissociated, and the free, dissociated components of the lipoprotein particles are contacted with a binding agent binding apoA-I. After washing away any unbound, free lipoprotein particle components, all that is theoretically left bound to the binding agent is free apoA-I apolipoprotein. Accordingly, the detection step should use a detection agent binding to apoA-I. The detection agent used to detect the intact lipoprotein particles comprising apoA-I isolated from the depleted sample may also be a detection agent binding apoA-I. However, since these lipoprotein particles are, in some embodiments, still intact, a detection agent binding another lipoprotein particle component may be used. In some embodiments, the detection agent used to detect the dissociated lipoprotein particle component(s) is identical to the detection agent used to detect the intact lipoprotein particles.

In some embodiments, the method further comprises a quantification and/or the calculation of ratios of lipoprotein particle abundance values as described above for protocol I.

Depletion of Lipoprotein Subpopulations

In some embodiments, a method is provided herein that comprises depleting a sample comprising lipoprotein particles of a certain type of lipoprotein particle before the sample is further processed. In some embodiments, such depletion may comprise depleting a sample of lipoprotein particles comprising a specific apolipoprotein, for example, an integral apolipoprotein, or a specific non-integral apolipoprotein. Such a depletion allows for a deconvolution of complex samples, which may be used, for example, to decrease undesired non-specific or background binding to a binding agent. In some embodiments, such a depletion also provides easy access to certain subpopulations of lipoprotein particles that could otherwise not readily be distinguished from other lipoprotein particles.

Depletion of a lipoprotein subpopulation is particularly useful, and sometimes necessary, for example, in embodiments aiming to determine the quantity of an analyte within a subpopulation of lipoprotein particles (e.g., apoA-I and apoC-III comprising lipoproteins) in comparison to the level of the analyte found in another subpopulation (e.g., apoA-I but not apoC-III comprising lipoproteins), where the quantity of the analyte is not detected by an immunological method, but, for example, by an enzymatic method. Accordingly, depletion of a lipoprotein subpopulation is particularly useful, for example, if a lipid analyte (e.g., cholesterol, or a triacylglycerol) is to be quantified.

For example, if the intent is to measure the concentration in HDL of apolipoproteins, proteins, or lipids that are present in both apoB-containing and apoA-I-containing lipoproteins, the sample may be first treated with reagents to precipitate apoB lipoproteins from the sample prior to the exposure of the sample to a binding agent, for example, a binding agent binding a non-integral apolipoprotein, thus eliminating apoB-lipoproteins from the sample. This can be achieved, for example, by the method of Finley, et al which uses dextran sulfate and magnesium chloride solutions (see Finley P R, Schifman R B, Williams R J, Lichti D A., *Cholesterol in high-density lipoprotein: use of Mg2+/dextran sulfate in its enzymic measurement.*, Clin Chem. 1978 June; 24(6):931-3., the entire contents of which are incorporated herein by reference). Additional suitable methods and reagents for depletion of specific lipoprotein particles or components will be apparent to those of skill in the art, and the disclosure is not limited in this respect.

Some aspects of this disclosure provide a method of detecting an analyte in or on a lipoprotein particle in a sample. In some embodiments, the method comprises (a) depleting the sample of any undesired lipoprotein particles; (b) contacting the sample with a binding agent that specifically binds a component of a lipoprotein particle, thereby depleting the sample of the component; (c) separating a lipoprotein particle bound to the binding agent of (b) from the remainder of the sample; and (d) subjecting a lipoprotein particle bound to the binding agent and/or a lipoprotein particle comprised in the remainder of the sample to an assay detecting the analyte. Depletion of undesired lipoprotein particles can be achieved by methods well known to those of skill in the art, for example, by immuno-precipitation methods or by binding of undesired particles to a solid support, e.g., via a binding agent that specifically binds an antigen characteristic of the undesired particles and that is immobilized on the solid support. The unbound fraction of the sample (now deplete of the undesired particles) can be removed from the support, resulting in a sample depleted of the undesired lipoprotein particles that can then be subjected to further processing.

An undesired lipoprotein particle may be any lipoprotein particle, or type of lipoprotein particle, that is not subject of the analysis in any given embodiment, or that would interfere with a measurement in a given embodiment. For example, in embodiments that focus exclusively on the analysis of HDL particles, LDL particles may be undesired lipoprotein particles. Such particles may be depleted before further processing of the sample, e.g., by immunoprecipitation using an antibody against apoB, which is comprised in LDL particles, but not in HDL particles. Vice versa, if the focus of an embodiment is solely on LDL particles, HDL particles may be depleted based on the presence of apoA-I in HDL, but not in LDL particles, and so forth. Additional subpopulation, for example, defined by the presence of an analyte, or of an apolipoprotein (e.g., as provided in Table 2), may be deemed undesired, and may be depleted according to methods provided herein or methods known to the skilled artisan. The disclosure is not limited in this respect. The depletion of undesired lipoprotein particles from a sample is particularly useful in embodiments in which an analyte is quantified via an assay that does not discriminate between desired and undesired lipoprotein particles as the source of the analyte, for example, in embodiments using an enzymatic assay to determine the quantity of a lipid (e.g. cholesterol or TAG) in specific lipoprotein subpopulations in a sample.

In an exemplary embodiment, the lipid content of HDL lipoprotein particles comprising apoC-III is determined and compared to the lipid content in HDL lipoprotein particles not comprising apoC-III, e.g., in lipoprotein particles in a plasma sample. Since the focus in this embodiment is on apoA-I-comprising HDL lipoprotein particles, LDL (apoB) particles can be discarded. Depletion of unwanted lipoprotein particles can be achieved by standard precipitation of such particles, for example, according to antibody precipitation methods well known to the skilled artisan. In an exemplary embodiment, to measure the concentration of cholesterol in HDL apo C-III lipoprotein particles, apoB-comprising lipoproteins are first removed from a plasma sample by standard precipitation methods. The remaining HDL lipoprotein particles are then contacted with a binding agent specifically binding apoC-III, e.g., in an ELISA plate well coated with an anti-apoC-III antibody. The unbound lipoprotein particles are removed from the well and transferred to another well, and both the bound HDL lipoprotein particles and the unbound HDL lipoprotein particles are subjected to a standard enzymatic cholesterol detection reagent. In this example, no further contacting of the unbound lipoprotein particles with another binding reagent is necessary.

Detection Assays

While detection and/or quantification of lipoprotein particles comprising an analyte of interest via ELISA is preferred in some embodiments, the instant disclosure is not limited to ELISA methodology. A binding agent may be conjugated to any suitable solid support and any suitable detection methodology may be used to detect and/or quantify any bound lipoprotein particles. For example, a binding agent may be conjugated to a bead or to the surface of a chip, e.g., in a lab-on-chip application. Beads with bound lipoprotein particles may be subjected to detection and/or quantification via a flow cytometry-type assay, e.g., by staining the bound lipoprotein particles with an antibody suitable for use in a FACS assay and performing a FACS assay on the stained beads.

Detection methodology suitable for use with the technology described herein will be apparent to those of skill in the art. In some embodiments, detection is via a solid phase enzyme immunoassay, for example, via an ELISA. Basic ELISA technology is well known in the art. While ELISA is often performed with an immunological binding agent, such as an antibody, ELISA technology is not so limited, and ligand binding assays using non-immuno binding agents, such as adnectins, aptamers, etc., can also be used. ELISA requires a binding agent that can be conjugated to a solid phase and a detection reagent that binds specifically to an analyte of interest. The detection agent is conjugated to an enzyme to generate a signal that is proportional to the abundance of the analyte and that can be detected and/or quantified. ELISA uses specialized plates that are optimized for optical detection of the signal produced by the respective enzyme. ELISA plates can be procured pre-coated with a binding agent of interest, or a binding agent, e.g., an antibody, can be conjugated on a per-assay basis.

One particularly useful type of ELISA in the context of lipoprotein detection and quantification according to aspects of this disclosure is sandwich ELISA. In some embodiments using sandwich ELISA, a solid surface, e.g., an ELISA plate well surface, is conjugated to, or "coated" with, a binding agent binding an analyte of interest, for example, with an antibody binding an apolipoprotein. A sample comprising the analyte is then contacted with the binding agent conjugated to the solid support surface under conditions allowing for the binding of the binding agent to the analyte. Any non-bound sample is removed and the solid support is washed under conditions allowing bound analyte to remain bound to the binding agent. A secondary binding agent is then added, which specifically binds an analyte of interest. That analyte may be the same or a different analyte as bound by the first binding agent. The result is an ELISA plate comprising the first binding agent, the secondary binding agent, and the analyte bound to both binding agents, or sandwiched between the binding agents. The secondary binding agent is then detected. The secondary binding agent may be detected by contacting it with a detection agent, or the secondary binding agent may be a detection agent in itself. For detection, a sandwich ELISA uses an enzymatic reaction that results in the emission of light or in the generation of a light-absorbing reaction product, for example, a horseradish peroxidase or luciferase reaction. Binding agents and detection agents useful for ELISA technology are well known to those of skill in the art, and many such reagents are commercially available. The enzyme reaction product is then measured, for example, via an ELISA plate reader, e.g., as the absorbency or fluorescence or electrochemical signal (e.g., current) of the respective plate well. In some embodiments, the signal is quantified.

While ELISA is a particularly suitable technology for use in connection with the described lipoprotein detection and quantification technology, other detection technologies that are suitable for use according to aspects of this disclosure will be apparent to those of skill in the art, including, for example, cytometry methods using binding agents conjugated to beads, and lab-on-chip applications. The disclosure is not limited in this respect.

In a lab-on-chip assay, a plurality of binding agents may be conjugated to the surface of a chip, for example, in a manner in which each binding agent is spatially separated from other binding agents. For example, a chip may contain an area in which an antibody against apoC-III is conjugated, an area in which an antibody against apoE is conjugated, an area in which an antibody against apoL is conjugated, and an area in which an antibody against apoA-I is conjugated, wherein each area is spatially separate from the other areas. Spatial separation may be achieved by conjugating each antibody as a distinct spot, or in distinct parts of a flow channel. In some embodiments, a biological sample is contacted with the chip under conditions suitable for the conjugated antibodies to bind lipoprotein particles comprising the respective analyte. In some embodiments, after the sample is removed from the chip, any bound lipoprotein particles are stained with an antibody specifically binding an analyte, for example, apoA-I, conjugated to a detection agent. The bound antibody can then be detected and/or quantified directly on the chip. In the example given above, the detected lipoprotein particles would be lipoprotein particles comprising apoC-III and apoA-I; apoE and apoA-I; apoL and apoA-I; and apoA-I but no apoC-III, apoE, or apoL.

The binding agent used for detection and/or quantification can be any binding agent suitable for a detection/quantification assay. Suitable binding agents, accordingly, include antibodies and antibody fragments that can be used in any suitable detection and/or quantification assay, such as an ELISA, FACS, or chip assay. Suitable detectable labels, accordingly, include, but are not limited to fluorescent moieties, e.g., fluorescent proteins (e.g., GFP, YFP, RFP, BFP, CFP, mCherry, etc.), or compounds (e.g., FITC, Cy3, Cy5, Alexa dyes, etc.), and enzymes catalyzing a reaction producing a measurable signal (e.g., HRP, luciferase, etc.). Suitable detectable labels will be apparent to those of skill in the art, and this disclosure is not limited in this respect.

Other analytes may be measured with enzymatic methods and reagents, for example, enzymatic methods and reagents for the quantification of blood lipids. As will be apparent to those of skill in the art, the measurement of lipoprotein lipids (cholesterol, cholesterol ester, triglyceride, phospholipids) is easily achieved with commercially available kits that employ enzymatic methods for quantifying the lipids. For example, cholesterol can be measured using the Infinity™ Cholesterol Liquid Stable Reagent from Thermo Electron Corp. according to the manufacturer's recommendations. The reagent and method is based on the methods described in Allain et al., *Enzymatic determination of total serum cholesterol.* Clin Chem. 1974 April; 20(4):470-5.), and modifications of Roeschlau et al. *Enzymatic determination of total cholesterol in serum.* Z Klin Chem Klin Biochem. 1974 May; 12(5):226.), with proprietary improvements to render the reagent stable in solution. Similarly, triacylglycerides can be measured using the Infinity™ Triglyceride Liquid Stable Reagent from Thermo Electron Corp. according to the manufacturer's protocol. The reagent and method is based on the method described in Wako (G Code No 997-69801); McGowan et al., *A peroxidase-coupled method for the colorimetric determination of serum triglycerides.*, Clin Chem. 1983 March; 29(3):538-42.) and Fossati, et al (Fossati P, Prencipe L., Serum triglycerides determined colorimetrically with an enzyme that produces hydrogen peroxide., Clin Chem. 1982 October; 28(10):2077-80.). The entire contents of each the references mentioned in this paragraph are incorporated herein by reference.

In some embodiments, an amount of a lipid is measured in the lipoproteins bound to a binding agent used in the methods provided herein, for example, in some embodiments using an ELISA plate comprising a binding agent binding to a non-integral apolipoprotein, a lipid may be measured in the lipoprotein bound to the ELISA plate, or an amount of lipid in a lipoprotein not bound to the plate. This measurement can be performed in analogy to a measurement of proteins (apolipoproteins or other proteins) in the bound and unbound lipoproteins, with the difference that the methods commonly used to measure lipids typically rely on enzymatic methods rather than immunological methods. Additional methods, enzymatic or other, suitable for the measurement of lipids in the context of lipoproteins will be apparent to the skilled artisan and it will be understood that the method is not limited in this respect.

Reagents and Kits

Some aspects of this disclosure provide reagents useful for use in the described methods. Kits comprising such reagents are also provided herein. For example, some embodiments provide an ELISA plate for detecting an apolipoprotein. The plate comprises, in some embodiments, one or more wells (e.g., 6, 12, 24, 96, or 384 wells), and a binding agent that specifically binds a non-integral apolipoprotein. In some embodiments, the binding agent is conjugated to a surface of the one or more wells of the ELISA plate. In other embodiments, the binding agent can be conjugated to the surface of the wells by incubating it under suitable conditions in the wells. The binding agent may be any binding agent specifically binding an analyte of interest, for example, an analyte as described in Table 2. In some embodiments, the ELISA plate comprises a plurality of wells that is conjugated to a plurality of different binding agents, for example, some wells comprising a binding agent that specifically binds a non-integral apolipoprotein (e.g., apoC-III) and other wells comprising a binding agent that specifically binds an integral apolipoprotein (e.g., apoA-I). In some embodiments, the binding agent is an antibody or an antibody fragment, for example, any of the antibodies described in Table 2.

In some embodiments, a kit is provided that comprises a plurality of ELISA plates, each conjugated to a binding agent specifically binding a different analyte of interest, for example, a different analyte as disclosed in Table 2. For example, in some embodiments, a kit is provided that comprises an ELISA plate comprising a binding agent conjugated to a binding agent specifically binding apoC-III and an ELISA plate comprising a binding agent conjugated to a binding agent specifically binding apoA-I.

In some embodiments, a kit as provided herein comprises additional reagents useful in a detection assay, for example, in an ELISA or a lab-on-chip assay. For example, in some embodiments, the kit comprises a detection agent that specifically binds an apolipoprotein; a detection agent that specifically binds to an integral apolipoprotein; and/or a detection agent that specifically binds to a non-integral apolipoprotein. In some embodiments, the kit further comprises a reagent, a buffer, an apolipoprotein standard, and/or a substrate useful in a detection assay, such as an ELISA or lab-on-chip assay. In some embodiments, the kit also comprises a reagent useful for dissociating a lipoprotein particle, for example, a detergent, such as TWEEN 20™.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Quantification of Lipoproteins with and without apoC-III

Apolipoprotein C-III (apoC-III) is a protein found on some apoB-containing or apoA-I-containing lipoproteins. It is not integral to the basic lipoprotein particle structure, thus particles exist both with and without apoC-III. ApoC-III itself increases adhesion of human monocytes to endothelial cells and activates pro-inflammatory molecules such as NFkB in these cells. ApoB-containing lipoproteins with apoC-III are enriched in TG and cholesterol and have slow clearance from plasma. Concentration of apoC-III in VLDL and LDL is highly and independently predictive of coronary heart disease, more so than TG alone. LDL with apoC-III, a remnant particle produced by partial lipolysis in plasma of VLDL with apoC-III, is the lipoprotein particle type most predictive for CVD in Type 2 diabetics and in US population samples. ApoC-III inhibits direct clearance of VLDL particles from plasma resulting in the formation of LDL. HDL-C with and without apoC-III showed opposite associations with the risk of CHD in a prospective study of apparently healthy men and women, therefore presence of apoC-III on HDL may be a useful marker of a dysfunctional form of HDL-C without cardioprotective benefits.

The currently used method for quantifying lipids and lipoproteins with and without apoC-III is both time-consuming and expensive. The protocol involves fractionation of lipoproteins into those containing apoC-III and those deficient of apoC-III using immuno-affinity chromatography. Plasma samples are incubated with Sepharose 4b resin beads coated with polyclonal anti-apoC-III antibody overnight at 4° C. The unbound apoC-III deficient fraction is eluted with multiple column volumes of phosphate-buffered saline, followed by elution of the bound apoC-III-containing fraction using multiple column volumes of 3M sodium thiocyanate. Elution with multiple column volumes results in a final sample many times diluted from plasma concentrations, requiring concentration of sample for the measurement of certain analytes, while the sodium thiocyanate interferes with the assays and must be removed from the apoC-III-containing fraction. Following fractionation, lipoprotein concentration is measured by ELISA while lipid concentration is measured by enzymatic assays. The time and cost of this assay is prohibitive for use in large epidemiological cohorts where the study of apoC-III would be of great value.

Described herein is a new technology and method to quantify the concentration of apoA-I, apoB, and cholesterol with and without apoC-III utilizing a modified sandwich ELISA protocol that is faster and less expensive than the current standard method. Lipoprotein complexes containing apoC-III are bound to 96-well ELISA plates coated with anti-apoC-III antibody. Unbound lipoproteins which are deficient in apoC-III remain in solution and are removed to a second 96-well ELISA plate, which is coated with either anti-apoA-I or anti-apoB antibody (as appropriate to the assay of choice) for quantification by standard sandwich ELISA assay. For the measurement of cholesterol, both the first and second 96-well plates are treated with enzymatic assay reagents for quantification.

In Protocol 1, bound lipoprotein complexes were incubated with either anti-apoA-I or anti-apoB secondary antibodies conjugated to HRP with subsequent addition of OPD to develop color, thus quantifying the apoA-I or apoB with apoC-III. In Protocol 2, bound lipoprotein complexes were dissociated with detergent and the freed apoA-I and apoB were quantified on a third 96-well ELISA plate by standard sandwich ELISA assay.

Protocol I

In this protocol, illustrated in FIG. 1, PLATE 1 captured apoC-III containing lipoproteins that remained bound and were measured directly on PLATE 1, while the unbound lipoproteins not containing apoC-III were transferred to a second plate (PLATE 2) for measurement.

Measurement of apoA-I with and without apoC-III:

Preparation:

A transparent 96-well plate was coated with 100 mcL per well of anti-apoA-I antibody at 0.005 mg/mL (recommended concentration 0.01 mg/mL-0.001 mg/mL) in the wells to be used for the calibration curve and with anti-apo-C-III antibody at 0.01 mg/mL (recommended concentration 0.01 mg/mL-0.001 mg/mL) in the wells to be used for the unknowns and assay control samples (Plate 1). A second transparent 96-well plate was coated with 100 mcL per well of anti-apoA-I antibody at 0.005 mg/mL (recommended concentration 0.01 mg/mL-0.001 mg/mL) (Plate 2). The plates are then blocked with 2% BSA or casein.

Binding of apoC-III-Containing Lipoproteins:

A 5-point standard curve was prepared from material with known apoA-I concentration diluted with 1× Phosphate Buffered Saline (PBS) containing 2% Bovine Serum Albumin (BSA) and 0.05% Tween 20 (recommended range from ~0.0001 mg/dL to ~0.001 mg/dL). In some embodiments, in order to reduce the risk of steric hindrance of the binding of the secondary antibody to apoA-I from apoB with apoC-III also binding to the anti-apoC-III plate, the unknown and assay control samples were first treated with Dextran Sulfate (50,000 g/mol)/Magnesium Chloride apoB precipitation reagent. Following centrifugation to pellet the apoB lipoproteins, the unknown and assay control samples were diluted with 1×PBS containing 0.5% BSA and no Tween 20 (recommended dilution 100×-10,000×). The standard curve dilutions were loaded at 100 mcL per well into the wells on Plate 1 that were coated with anti-apoA-I antibody. The assay control and unknown sample dilutions were loaded at 100 mcL per well into the wells on Plate 1 that were coated with anti-apoC-III antibody. The standard curve, assay control, and unknown samples should be loaded in triplicate. The plate was incubated in a sealed container with damp towels for 1-3 hours at 37° C.

Transfer of Unbound apoA-I:

For assay control and unknown samples, the sample liquid in the wells of PLATE 1 was gently mixed by aspiration and dispensing without creating bubbles and transferred to corresponding dilution tubes. These samples were diluted 50,000× with 1×PBS containing 2% BSA and 0.05% Tween 20 (recommended dilution 1000× to 100, 000×). A 5-point standard curve was prepared from material with known apoA-I concentration diluted with 1× Phosphate Buffered Saline (PBS) containing 2% Bovine Serum Albumin (BSA) and 0.05% Tween 20 (recommended range from ~0.0001 mg/dL to ~0.001 mg/dL). The standard curve, assay control, and unknown sample dilutions were loaded at 100 mcL per well into Plate 2 in triplicate. The plate was incubated in a sealed container with damp towels for 1-3 hours at 37° C. As Plate 2 incubates, Plate 1 is stored at 4° C.

Addition of Secondary Antibody Conjugated to HRP:

For Plate 1, anti-apoA-I antibody conjugated to HRP was diluted to 0.005 mg/mL (recommended concentration 0.005 mg/mL-0.0005 mg/mL) with 1×PBS containing 0.5% BSA. For Plate 2, anti-apoA-I antibody conjugated to HRP was diluted to 0.005 mg/mL (recommended concentration 0.005 mg/mL-0.0005 mg/mL) with 1×PBS containing 2% BSA and 0.05% Tween 20. When Plate 2 completed incubation, Plate 1 was washed with 1×PBS and Plate 2 was washed with 1×PBS containing 0.1% Tween 20. The appropriate HRP solution was loaded at 100 mcL into all wells that contain standard curve, assay control, and unknown samples. The plates were incubated together in a sealed container with damp towels for 1-3 hours at 37° C.

Addition of Substrate:

Both Plate 1 and Plate 2 were washed as described previously. While plates are being washed, fresh o-Phenylenediamine (OPD) solution was prepared. When ready, 160 mcL of OPD solution were added into all wells that contain standard curve, assay control, and unknown samples. Plates were monitored by periodic readings taken at 450 nm in a 96-well ELISA plate reader. Data was saved when the absorbance for highest point on the calibration curve is around 0.800.

Figure 2:
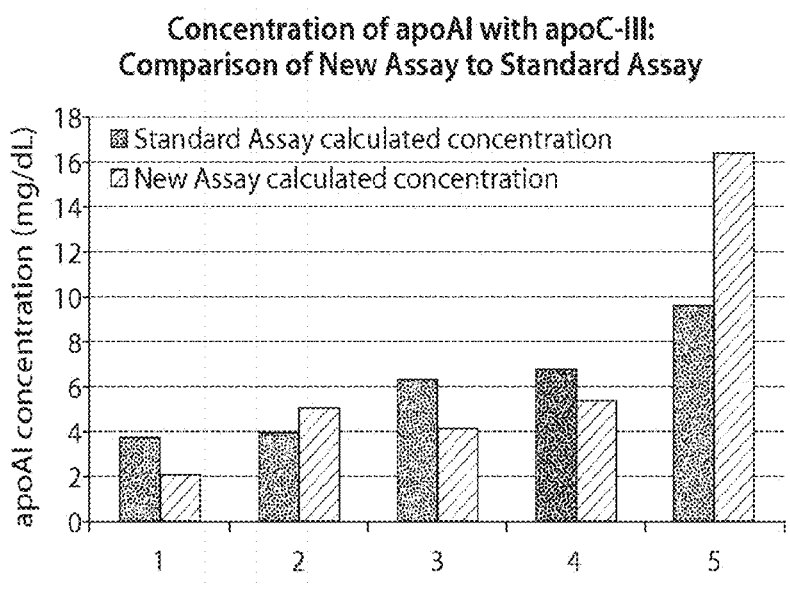
FIG. 2. Comparison of data obtained using Protocol I to data obtained using a standard immuno-affinity protocol.

FIG. 1 illustrates the procedure described above. FIG. 2 shows a comparison of data obtained using a conventional immuno-affinity based method to data obtained from the same samples using the instantly described method. The data showed good correlation between the two methods, suggesting that the assay described herein is functional.

Measurement of apoB with and without apoC-III:

The method was also successfully carried out as described above, but with the following differences: The precipitation of apo-B from samples was eliminated and Plate 2 was coated with anti-apoB antibody at a 0.005 mg/mL concentration (recommended concentration range of 0.005 mg/mL-0.0005 mg/mL). The recommended sample dilution for Plate 1 is 2000×. The recommended sample dilution for Plate 2 is 8000×. The recommended Assay Control A dilution for Plates 1 and 2 is 8000×. It is also recommended to use anti-apoB/HRP conjugate at concentrations of 0.001 mg/mL (recommended concentration range of 0.001 mg/mL-0.0001 mg/mL) on Plate 1 and Plate 2.

Protocol II

In this protocol, PLATE 1 was used to fractionate lipoproteins containing apoC-III from those without apoC-III. Unbound lipoproteins were transferred to PLATE 2 for measurement. Tween was used to disrupt the lipoprotein complexes in PLATE 1 and the solubilized proteins were transferred to PLATE 3 for quantification.

Measurement of apoA-I with and without apoC-III:

Preparation:

A transparent 96-well plate was coated with 100 mcL per well of anti-apo-C-III antibody at 0.005 mg/mL (recommended concentration 0.01 mg/mL-0.001 mg/mL) (Plate 1). Two transparent 96-well plates were coated with 100 mcL per well of anti-apoA-I antibody at 0.01 mg/mL (recommended concentration 0.01 mg/mL-0.001 mg/mL) (Plate 2 and Plate 3). The plates were then blocked with 2% BSA or casein.

Binding of apoC-m-Containing Lipoproteins:

A calibration curve ranging from 0.004 mg/dL-0.00006 mg/dL of apoC-III (recommended range 0.001 mg/dL-0.00001 mg/dL) was prepared from a calibrated plasma pool. The unknown and assay control samples were diluted with 1×PBS containing 0.5% BSA and no Tween 20 to 50,000× (recommended dilution 100×-100,000×). The calibration curve, assay control and unknown sample dilutions were loaded at 100 mcL per well into Plate 1 in triplicate. The plate was sealed with an adhesive cover and incubated for 1-3 hours at 37° C.

Transfer of Unbound apoA-I:

The sample liquid in the unknown and assay control sample wells of PLATE 1 was gently mixed by aspiration and dispensing without creating bubbles and transferred to corresponding dilution tubes. These calibration curve, unknown, and assay control samples were diluted with 1×PBS containing 2% BSA and 0.05% Tween 20 by 10× to produce a final dilution of the unknown and assay control samples of 500,000× (recommended dilution 10,000× to 1,000,000×). The standard curve, assay control, and unknown sample dilutions were loaded at 100 mcL per well into Plate 2 in triplicate. The plate was sealed with an adhesive cover and incubated for 1-3 hours at 37° C. Dissociation of lipoproteins bound to Plate 1: While Plate 2 incubated, Plate 1 was washed with 1×PBS containing 0.5% BSA and no Tween 20. A mixture of 1×PBS containing 0.5% BSA and 0.2% Tween 20 was loaded at 125 mcL to all wells of Plate 1 containing sample. Plate 1 was then sealed with an adhesive cover and incubated for 1-3 hours at 37° C. 100 mcL of the sample liquid in all the wells of PLATE 1 was gently mixed by aspiration and dispensing without creating bubbles and transferred in its entirety to corresponding wells in Plate 3. The plate was sealed with an adhesive cover and incubated for 1-3 hours at 37° C. As Plate 3 incubates, Plate 2 was stored at 4° C.

Addition of Secondary Antibody Conjugated to HRP:

Anti-apoA-I antibody conjugated to HRP at 0.005 mg/mL (recommended concentration 0.005 mg/mL-0.0005 mg/mL) was prepared for Plates 2 using 1×PBS containing 2% BSA and 0.05% Tween 20. To improve sensitivity of detection on Plate 3, anti-apoA-I antibody conjugated to Biotin was prepared at 0.001 mg/mL (recommended concentration 0.001 mg/mL-0.0001 mg/mL). When Plate 3 completed incubation, both plates were washed with 1×PBS containing 0.1% Tween 20. The HRP solution was loaded at 100 mcL into all wells that contain standard curve, assay control, and unknown samples on Plate 2. The Biotin solution was loaded at 100 mcL into all wells that contain standard curve, assay control, and unknown samples on Plate 3. The plates were sealed with an adhesive cover and incubated for 1-3 hours at 37° C. During incubation, a 100,00× dilution of avidin peroxidase was prepared for incubation on Plate 3. Following incubation, Plate 3 was washed with 1×PBS containing 0.1% Tween 20. The avidin-peroxidase solution was loaded at 100 mcL into all wells that contain standard curve, assay control, and unknown samples. Plate 3 was sealed with an adhesive cover and incubated for 1-3 hours at 37° C.

Addition of Substrate:

Both plates were washed as described previously. While plates were being washed, fresh o-Phenylenediamine (OPD) solution was prepared. When ready, 200 mcL of OPD solution was added into all wells that contained standard curve, assay control, and unknown samples. Plates were monitored by periodic readings taken at 450 nm in a 96-well ELISA plate reader. Data was saved when the absorbance for highest point on the calibration curve is around 0.800.

Measurement of apoB with and without apoC-III:

The method was carried out as described above, but with anti-apoB antibody as the primary antibody at 0.005 mg/mL concentration (recommended concentration range 0.001 mg/mL-0.0001 mg/mL) and anti-apoB/HRP conjugate at 0.001 mg/mL (recommended concentration 0.001 mg/mL-0.0001 mg/mL).

FIG. 3 shows an illustration of the method described above.

Figure 4:
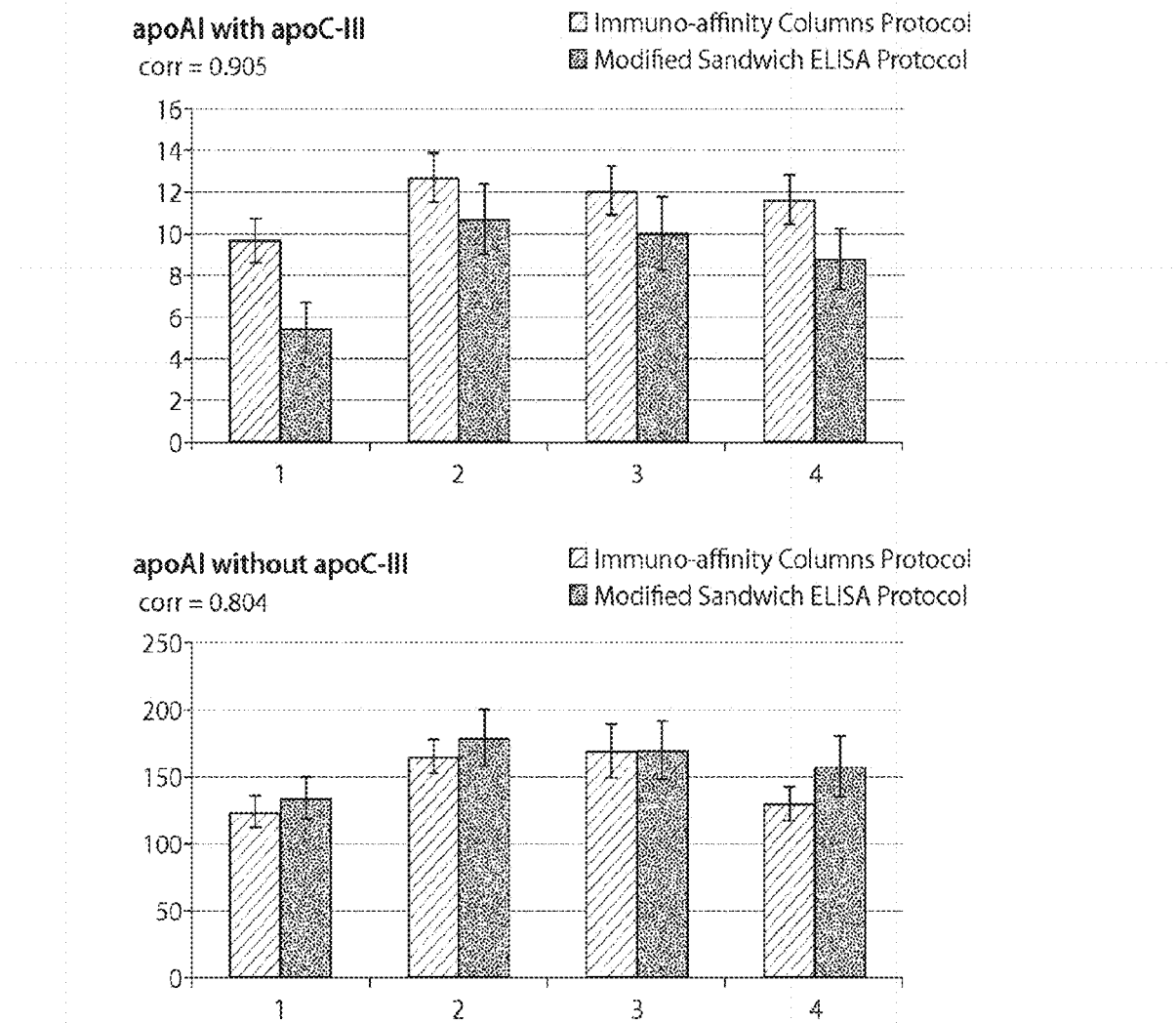
FIG. 4. Data obtained using Protocol II.

FIG. 4 shows the concentrations (with standard errors) of apoA-I with and without apoC-III obtained from four human plasma samples comparing the immuno-affinity protocol to the modified sandwich ELISA protocol (n=6).

Comparison of Measurements Obtained with the Technology Provided Herein with Measurements Obtained from the Current "Gold Standard" Immuno-Affinity Method.

Experimental Design:

The protocol used for measuring according to the instantly provided technology was as outlined in FIG. 3.

Equipment:
Serological PipetAid
Single-channel, Multi-channel pipettemen, various volumes
Plate washer: Bio-Tek Model: 405TS
Plate reader Bio-Tek Model: Synergy
Plate rocker VWR Rocking Platform
Materials:
Greiner bio-one high-binding microtiter plates, for coating ELISA plates, Greiner, Cat#655081
Greiner bio-one non-binding microtiter plates, for Intermediate dilutions in ELISA, Greiner, Cat#655101
Blocking buffer: Casein in PBS, ThermoSci, Cat#37528
50 nL conical tubes: VWR. Cat#21008-178
15 mL conical tubes: VWR, Cat#62406-200
5 mL tubes: Falcon tubes, VWR, Cat#60819-138
10 mL serological pipet: VWR, Cat#89130-888
Reagent reservoirs: 25 mL polystyrene, Corning, Cat#8095
Acetate plate sealers: Corning, VWR, Cat#62402-921
Tween-20, SIGMA, Cat#P1379-500ML
Reagents:
Twice distilled, nanofiltered water
Bovine, Sera Albumin: SIGMA, Cat#A3803-100G
10×PBS, Omni-Pur, VWR, Cat#6505-4L
Avidinperoxidase, SIGMA. Cat#A7419
OPD, o-Phenylenediamine dihydrochloride tablets, SIGMA, Cat#P9187-50set
Coating, Goat Anti-human ApoAI: Academy BioMedical, Cat#11A-G2b
Coating, Rabbit Anti-human ApoCIII: Academy BioMedical, Cat#33A-R1b
Detection, Goat Anti-human ApoAI-Biotinylated: Academy BioMedical, Cat#11B-G2b
Detection, Goat Anti-human ApoCIII-HRP conjugated: Academy BioMedical, Cat#33H-G2b
Standard ELISA Wash Buffer: 1×PBS/0.1% Tween-20
Gentle ELISA Wash Buffer: 1×PBS
ELISA Diluent: 2% BSA/1×PBS/0.05% Tween-20
Sample Diluent: 0.5% BSA/1×PBS
Coating/Blocking Procedure:
Anti-ApoAI plates
1. Coat Greiner bio-one high-binding microtiter plates with 100 µl of 0.005 mg/mL of Goat Anti-Human ApoAI antibody.
2. Incubate for 60 minutes at 37° C.±2° C.
3. Wash plate 3 times with Standard ELISA Wash Buffer
4. Block with 200 µl of Casein blocking buffer
5. Incubate for 60 minutes at 37° C.±2° C.
6. Wash plate 3 times with Standard ELISA Wash Buffer
7. Store plates at 2-8° C. with an expiry of 2 weeks
Anti-ApoCIII Plates
1. Coat Greiner bio-one high-binding microtiter plates with 100 µl of 0.01 mg/mL of Rabbit Anti-Human ApoCIII antibody.
2. Incubate for 60 minutes at 37° C.±2° C.
3. Wash plate 3 times with Standard ELISA Wash Buffer
4. Block with 200 µl of Casein blocking buffer
5. Incubate for 60 minutes at 37° C.±2° C.
6. Wash plate 3 times with Standard ELISA Wash Buffer
7. Store plates at 2-8° C. with an expiry of 2 weeks
Tandem ELISA Procedure:
Plate 1 (P1) Anti-ApoCIII Coated Plate for ApoCIII Detection
1. Warm the Anti-ApoCIII coated plate to Room Temperature
2. Prepare Standard Curve with Green2010, with Sample Diluent, according to Table 3 below.

TABLE 3

| Green N2010 Titration for Standard Curve | | | | | 1:2 |
|---|---|---|---|---|---|
| ApoC3 | Volume of sample | Sample | Volume of Diluent | Total Volume | Dilution | Total Dilution |
| primary | 20 | neat | 1980 | 2000 | 100 | 100 |
| S1 | 100 | primary | 1900 | 2000 | 20 | 2,000 |
| S2 | 500 | S1 | 500 | 1000 | 2 | 4,000 |
| S3 | 500 | S2 | 500 | 1000 | 2 | 8,000 |
| S4 | 500 | S3 | 500 | 1000 | 2 | 16,000 |
| S5 | 500 | S4 | 500 | 1000 | 2 | 32,000 |
| S6 | 500 | S5 | 500 | 1000 | 2 | 64,000 |
| S7 | 500 | S6 | 500 | 1000 | 2 | 128,000 |

3. Prepare Yellow, Red, Green & Blue 2010, with Sample Diluent, according to Table 4 below

TABLE 4

| Yellow, Red, Green and Blue N2010 Samples | | | | | |
|---|---|---|---|---|---|
| Sample ID | Dilution | Volume (ul) | Sample Source | Diluent vol. (ul) | Total Volume (uL) | Total Dilution |
| A | 100 | 20 | Neat tube | 1980 | 2000 | 100 |
| 10k | 100 | 20 | A | 1980 | 2000 | 10,000 |
| 200k | 2 | 1000.0 | 10k | 1000.0 | 2000 | 20,000 |

4. Prepare samples with Sample Diluent, according to Table 5 below

TABLE 5

| Samples | | | | | |
|---|---|---|---|---|---|
| Sample ID | Dilution | Volume (ul) | Sample Source | Diluent vol. (ul) | Total Volume (uL) | Total Dilution |
| A | 100 | 20 | Neat tube | 1980 | 2000 | 100 |
| 10k | 100 | 20 | A | 1980 | 2000 | 10,000 |
| 200k | 2 | 1000 | 10k | 1000 | 2000 | 20,000 |

5. Pipet 100 uL of each Sample in triplicate on the plates according to Table 6

TABLE 6

| P1 | 1 | 2 | 3 | 4 | 5 | 6 | 7 | 8 | 9 | 10 | 11 | 12 |
|---|---|---|---|---|---|---|---|---|---|---|---|---|
| A | C3 Std Crv 1 | C3 Std Crv 1 | C3 Std Crv 1 | Yellow 2010 | Yellow 2010 | Yellow 2010 | Sample 5 | Sample 5 | Sample 5 | Sample 13 | Sample 13 | Sample 13 |
| B | C3 Std Crv 2 | C3 Std Crv 2 | C3 Std Crv 2 | Red 2010 | Red 2010 | Red 2010 | Sample 6 | Sample 6 | Sample 6 | Sample 14 | Sample 14 | Sample 14 |

TABLE 6-continued

| P1 | 1 | 2 | 3 | 4 | 5 | 6 | 7 | 8 | 9 | 10 | 11 | 12 |
|---|---|---|---|---|---|---|---|---|---|---|---|---|
| C | C3 Std Crv 3 | C3 Std Crv 3 | C3 Std Crv 3 | Green 2010 | Green 2010 | Green 2010 | Sample 7 | Sample 7 | Sample 7 | Sample 15 | Sample 15 | Sample 15 |
| D | C3 Std Crv 4 | C3 Std Crv 4 | C3 Std Crv 4 | Blue 2010 | Blue 2010 | Blue 2010 | Sample 8 | Sample 8 | Sample 8 | Sample 16 | Sample 16 | Sample 16 |
| E | C3 Std Crv 5 | C3 Std Crv 5 | C3 Std Crv 5 | Sample 1 | Sample 1 | Sample 1 | Sample 9 | Sample 9 | Sample 9 | Sample 17 | Sample 17 | Sample 17 |
| F | C3 Std Crv 6 | C3 Std Crv 6 | C3 Std Crv 6 | Sample 2 | Sample 2 | Sample 2 | Sample 10 | Sample 10 | Sample 10 | Sample 18 | Sample 18 | Sample 18 |
| G | C3 Std Crv 7 | C3 Std Crv 7 | C3 Std Crv 7 | Sample 3 | Sample 3 | Sample 3 | Sample 11 | Sample 11 | Sample 11 | Sample 19 | Sample 19 | Sample 19 |
| H | Blank | Blank | Blank | Sample 4 | Sample 4 | Sample 4 | Sample 12 | Sample 12 | Sample 12 | Sample 20 | Sample 20 | Sample 20 |

6. Seal plate with Acetate Plate sealer. Incubate plate at Room Temperature for 60 minutes. During incubation, warm ELISA Diluent to Room Temperature 7. Post 60 minute incubation, create final dilutions for P2 plate, using ELISA Diluent. See Table 7 below

TABLE 7

Standard Curve, YRGB and Sample Dilutions for INTERMEDIATE plate

| Sample ID | Dilution | Volume (ul) | Sample Source | Diluent vol. (ul) | Total Volume (ul) | Total Dilution |
|---|---|---|---|---|---|---|
| YRGB | 20 | 10 | P1 plate | 190 | 200 | 400,000 |
| S1–S7 | 10 | 10 | P1 plate | 90 | 100 | 10 |
| Samples | 20 | 10 | P1 plate | 190 | 200 | 400,000 |

Standard Curve, YRGB and Sample Dilutions for P2 plate

| Sample ID | Dilution | Volume | Sample | Diluent vol. | Total | Total Dilution |
|---|---|---|---|---|---|---|
| YRGB | 10 | 10 | Intermediate | 90 | 100 | 4,000,000 |
| S1–S7 | 10 | 10 | Intermediate | 90 | 100 | 100 |
| Samples | 10 | 10 | Intermediate | 90 | 100 | 4,000,000 |

This ELISA uses 3 independent ELISA plates used in tandem.

8. Post 60 minute incubation of P1, proceed to Step 9 for P2. The following sub steps of Step 8 are for Plate 1 (P1) only. Step 8.c instructs the creation of plate P3. Plate 1 (P1) is washed using Gentle Wash Buffer (1×PBS)

a. Post creation of P2 (Step 9-11), Wash P1 plate on plate washer using program "3×WASH" with 1×PBS b. DISSOCIATION: Pipette 125 μl of ELISA Diluent to all wells on P1 plate c. Seal plate with Acetate Plate sealer. Incubate plate at Room Temperature for 60 minutes on plate rocker. Set rocker to 7.

During P1 incubation, warm Plate 3 (P3), an Anti-ApoAI coated plate, to room temperature d. Post P1 dissociation incubation, Pipette 100 μl of samples from P1 wells directly to the same position on plate P3 wells P1, P2 and P3 are now running in tandem. To continue with P3 ELISA, proceed to Step 26.

e. Post creation of P3, Wash P1 plate on plate washer using program "3×WASH" with 1×PBS f. Create Apo-CIII-BioTin secondary antibody according to the specific ApoCIII-BioTin Table 8

TABLE 8

ApoC3-HRP Dilutions

| | | | Primary Dilution | | | | Secondary Dilution | | | |
|---|---|---|---|---|---|---|---|---|---|---|
| | | Total Dilution | x for Dil 1 | Volume of Anti-Apoc3 | Volume of PBS | Total Volume | x for Dil 2 | Volume of Primary Dilution | Volume of PBS | Total Volume |
| ApoC3-HRP | 1 Plate | 1250 | 10 | 40 | 360 | 400 | 125 | 176 | 21,824 | 22,000 Use 1xPBS for Dilution | g. Pipette 100 µl of ApoCIII-HRP antibody to all wells on the P1 detection plate
h. Seal plate with Acetate Plate sealer. Incubate plate at 37° C.±2° C. for 60 minutes. NOTE: 45 minutes into the incubation, create OPD according to Table 9 below
i. Post 80 minute incubation, read on Bio-Tek spectrophotometer using ELISA software protocol
j. Save data file
k. Export data file and submit for data analysis Plate 2 (P2) Anti-ApoAI Coated; Detection of ApoAI with No CIII 9. Pipette 190 µl of ELISA Diluent (ED) to all sample and YRGB wells. Pipette 90 µl of ELISA Diluent (ED) to all Standard Curve wells in Intermediate plate. Pipette 90 µl of ELISA Diluent (ED) to all wells on P2 plate.
10. Pipette 10 µl of all Standard Curve wells from P1 into 90 µl of ELISA Diluent in Intermediate plate. Mix sample by pipetting up and down ten times. Pipette 10 µl of all YRGB and Sample wells from P1 into 190 µl of ELISA Diluent in Intermediate plate, then transfer 10 µl from all wells of the Intermediate plate to P2 plate. Mix by pipetting up and down ten times.
11. Seal plate with Acetate Plate sealer. Incubate plate at 37° C.±2° C. for 60 minutes
12. Wash P2 with Standard ELISA Wash Buffer using plate washer program "3× Wash"
13. Create ApoA1-Biotinylated secondary antibody according to the specific ApoA1 secondary Table 9

TABLE 9

ApoA1-Biotinylated Dilutions

| | total x | x for Dilution | Volume of Antibody (uL) | Volume of 1xPBS (uL) | Total Volume (mL) | Number of Plates |
|---|---|---|---|---|---|---|
| ApoA1-BioTinylated | 1000x | 1000 | 11.0 | 10,989.0 | 11 | 1 |

14. Add 100 µl ApoA1-Biotinylated Conjugate antibody to all wells on the P2 detection plate
15. Seal plate with Acetate Plate sealer. Incubate plate at 37° C.±2° C. for 60 minutes
16. Wash P2 with Standard ELISA Wash Buffer using plate washer program "3× Wash"
17. Create Avidinperoxidase according to Table 10 below

TABLE 10

Create Avidin Peroxidase Final 1:100k in 1xPBS

| Avidin Peroxidase | Volume (ul) | Sample Source | Diluent vol. (ul) | Total Volume (uL) | Total Dilution |
|---|---|---|---|---|---|
| 100x | 10 | Avidin | 990 | 1000 | 100 |
| 1000x | 20 | 100x | 19,980 | 20,000 | 10000 |

18. Add 100 µl of Avidinperoxidase to the ApoA1-Biotinylated wells on the P2 detection plate
19. Seal plate with Acetate Plate sealer. Incubate plate at 37° C.±2° C. for 60 minutes. NOTE: 45 minutes into the incubation, create OPD according to Table 9 below

TABLE 11

Create OPD

| ddH20 | Gold Tablet | Silver Tablet | Volume Total |
|---|---|---|---|
| 20 mL | 1 | 1 | 20 mL |

Shake and vortex tablets in water until tablets have completely dissolved

20. Wash P2 with Standard ELISA Wash Buffer using plate washer program "3× Wash"
21. Pipette 200 µl per well of OPD solution to entire plate
22. Seal plate with Acetate plate sealer, Incubate for 80 minutes at room temperature in the dark.
23. Post 80 minute incubation, read on Bio-Tek spectrophotometer using ELISA software protocol.
24. Save data file
25. Export data file and submit for data analysis.

Plate 3 (P3) Anti-ApoAI Coated; Detection of ApoAI with CIII

26. Plate contains 100 µl of samples from P1 (post dissociation incubation)
27. Seal plate with Acetate Plate sealer. Incubate plate at 37° ° C.±2° C. for 60 minutes
28. Wash P2 with Standard ELISA Wash Buffer using plate washer program "3× Wash"
29. Create Avidinperoxidase according to Table 10
30. Add 100 µl of Avidinperoxidase to the ApoA1-Biotinylated wells on the P3 detection plate
31. Seal plate with Acetate Plate sealer. Incubate plate at 37° C.±2° C. for 60 minutes. NOTE: 45 minutes into the incubation, create OPD according to Table 11
32. Wash P3 with Standard ELISA Wash Buffer using plate washer program "3× Wash"
33. Pipette 200 µl per well of OPD solution to entire plate
34. Seal plate with Acetate plate sealer, Incubate for 80 minutes at room temperature in the dark.
35. Post 80 minute incubation, read on Bio-Tek spectrophotometer using ELISA software protocol.
36. Save data file
37. Export data file and submit for data analysis Data Analysis Raw data from the spectrophotometer are entered into Excel for analysis. The standard curve is fit with a 3-parameter analysis. Sample data and controls are interpolated from the linear range of the standard curve. All triplicate points of the curve, controls and samples must have a percent CV that is less than or equal to 15%. Blank wells of the standard curve must read ≤0.200 OD.

Results

We measured 100 samples with the protocol provided above, 53 of whom were cases of Myocardial Infarction and 47 of whom were controls. All lab staff were blinded to case/control status. A logistic regression model was run that included HDL with apoAI and with apoC-III (Apo AI(CIII+)), HDL with apoAI and without apoC-III (Apo AI(CIII−)), and gender as risk factors or protective factors.

Gender was included based on gender being a risk factor in cardiovascular disease (risk is lower in women than in men).

Using the instantly provided protocol, the following results were obtained:

|  | Point Estimate | Confidence Interval (Lower, Upper) | Risk or Protection? |
|---|---|---|---|
| Apo AI(CIII−) | 0.978 | (0.959, 0.998) | PROTECTIVE |
| Apo AI(CIII+) | 1.786 | (1.007, 3.168) | RISK FACTOR FOR MI |
| gender | 0.203 | (0.079, 0.522) | |

Using the "gold standard" immuno-affinity method, the following results were obtained from the same samples:

|  | Point Estimate | Confidence Interval (Lower, Upper) | |
|---|---|---|---|
| Apo AI(CIII−) | 0.985 | (0.973, 0.996) | PROTECTIVE |
| Apo AI(CIII+) | 1.253 | (1.107, 1.419) | RISK FACTOR FOR MI |
| gender | 0.193 | (0.070, 0.530) | |

The data show that the instantly provided methods provide stronger point estimates and a lower error as compared to the gold standard.

CONCLUSION

The data show that the modified sandwich ELISA assay proposed here produced data that meet or exceed the precision and accuracy of the existing immuno-affinity protocol, the current "gold standard" for this field of research. The approach described herein produces data that correlate well with and provides concentration measurements that are in agreement with the previously known methods, yet is simpler, quicker, and more cost effective.

All publications, patents, and database entries mentioned herein are hereby incorporated by reference in their entirety as if each individual publication, patent, or database entry was specifically and individually indicated to be incorporated by reference. In case of conflict, the present application, including any definitions herein, will control.

While specific, non-limiting, exemplary embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

What is claimed is:

1. A method of detecting an apolipoprotein in a sample, the method comprising
   (a) contacting a sample comprising a lipoprotein particle with a first binding agent, wherein the lipoprotein particle comprises an integral apolipoprotein and may or may not also comprise a non-integral apolipoprotein, wherein the first binding agent specifically binds a non-integral apolipoprotein on the lipoprotein particle, and wherein the first binding agent is selected from the group consisting of antibody, antibody fragment, aptamer and adnectin;
   (b) removing the sample of (a) from contact with the first binding agent bound to the non-integral apolipoprotein-containing lipoprotein particle;
   (c) contacting the sample of (b) with a second binding agent that specifically binds an integral apolipoprotein, wherein the second binding agent is selected from the group consisting of antibody, antibody fragment, aptamer and adnectin;
   (d) dissociating the non-integral apolipoprotein-containing lipoprotein particle of (a) into two or more dissociated components, wherein the dissociated components comprise i) the integral apolipoprotein and ii) the first binding agent of (a) bound to the non-integral apolipoprotein;
   (e) contacting the dissociated components of (d) with a third binding agent that specifically binds an integral apolipoprotein, wherein the third binding agent is selected from the group consisting of antibody, antibody fragment, aptamer and adnectin; and
   (f) detecting an apolipoprotein in or on a lipoprotein particle bound to the second binding agent of (c) and/or an apolipoprotein bound to the third binding agent of (e).

2. The method of claim 1, wherein the non-integral apolipoprotein is selected from the group consisting of apoA-II, apoA-IV, apoA-V, apoC-I, apoC-II, apoC-III, apoC-IV, apoD, apoE, apoH, apoJ, apoL-I, apoM, apoF, LCAT (phosphatidylcholine-sterol acyltransferase), CETP, PL transfer protein, SAA1, SAA2, SAA4, PON1, PON3, Complement C3, α-1-acid glycoprotein 2, α-2-HS glycoprotein, α-1-antitrypsin, α-1B-glycoprotein, Fibrinogen (alpha-chain), Serotransferrin, Haptoglobin-related protein, Transthyretin, Vitamin D-binding protein, apoB-100, Serum albumin, Complement C4B, Complement C4A, Complement C9, Vitronectin, α-2-antiplasmin, α-1-microglobulin/bikunin, Inter-a-trypsin inhibitor H4, Angiotensinogen, Serpin peptidase inhibitor, Kininogen-1, Plasma retinol-binding protein, Prenylcysteine oxidase, Hemopexin, α-1-acid glycoprotein 1, Gelsolin, zinc α-2 glycoprotein, hemoglobin subunit beta, pigment epithelium derived factor, α-1-antichymotrypsin, heparin cofactor 2, antithrombin III, complement B, Prothrombin, aminopeptidase N, hemoglobin subunit alpha, catheliciden antimicrobial peptide, leucine-rich α-2 glycoprotein, phosphatidylinositol-glycan-specific phospholipase D, Inter-a-trypsin inhibitor H2, band 3 anion transport protein, carbonic anhydrase 1, N-acetylmuramoyl-L-alanine amidase, β-2-microglobulin, filamin-A, Fibronectin, integrin α-II-b, thrombospondin I, complement C1s subcomponent, Lumican, Afamin, Lipoprotein Associated Phospholipase A2 (PAF-AH), hemoglobin binding protein, apo (a), apoB, and platelet basic protein.

3. The method of claim 1, wherein the integral apolipoprotein is selected from the group consisting of apoA-I and apoB.

4. The method of claim 1, wherein the second binding agent of (c) and the third binding agent of (e) are identical.

* * * * *